United States Patent [19]

Tubaro et al.

[11] Patent Number: 5,281,702

[45] Date of Patent: Jan. 25, 1994

[54] DI-N-DEACETYL-LYSOGANGLIOSIDES

[75] Inventors: Ezio Tubaro; Giovanni Cavallo, both of Rome, Italy

[73] Assignee: Wellcome Foundation Limited, London, England

[21] Appl. No.: 689,901

[22] PCT Filed: Dec. 27, 1990

[86] PCT No.: PCT/GB90/02028

§ 371 Date: Jun. 18, 1991

§ 102(e) Date: Jun. 18, 1991

[87] PCT Pub. No.: WO91/09603

PCT Pub. Date: Jul. 11, 1991

[30] Foreign Application Priority Data

Dec. 28, 1989 [IT] Italy ............................ 48702 A/89

[51] Int. Cl.$^5$ .................. C07H 5/06; C07H 15/04; A61K 31/73

[52] U.S. Cl. .......................... 536/53; 536/4.1; 536/55; 536/55.1; 536/55.2; 514/25; 514/54; 514/62

[58] Field of Search ............... 536/4.1, 53, 55, 55.1, 536/55.2; 514/25, 54, 62; 435/198

[56] References Cited

FOREIGN PATENT DOCUMENTS 0036372 7/1984 European Pat. Off. .
0321287 6/1989 European Pat. Off. .
0328420 8/1989 European Pat. Off. .

OTHER PUBLICATIONS

Nores et al; Carbohydrate Research 179:393–410 (1988).
Song et al; Biochemistry 28:4194–4200 (1989).
Manev et al; Journal of Pharmacology and Experimental Therapeutics 252(1):419–427 (Jan. 1990).
Chemical Abstracts, vol. 113, No. 1, abstract 151b, Dyatlovitskaya et al, Derivatives of ganglioside GM3 and their immounomodullating effects, Jul. 2, 1980.
Isolation of Cholera Toxin by Affinity Chromatography on Porous Silica Beads with Covalently Coupled Galgliodise GM1, Taylot & Tardy, Institute Merieux, pp. 471–478 (1980).
Synthesis of Lysogangliodides, Neuenhofer, et al., Biochemistry, 24, pp. 525–532 (1985).
Chemical Abstracts, 113, No. 1, p14 (1990).
Preparation of GM1 ganglioside molecular species having homogeneous fatty acid and long chain base moieties, Sonnino et al., J. of Lipid Research, 26, pp. 248–257 (1985).
Bioorganic Chemistry, Dyatlovitskaya et al., 16, 402 (1990) in Russian (translation attached).
Holmgren et al, Medical Biology, 52 229, (1974).
Taketomi and Kawamura, J. Biochem., 68 475 (1970).

Primary Examiner—Nancy S. Carson
Attorney, Agent, or Firm—Nixon & Vanderhye

[57] ABSTRACT

The invention relates to N-deacetyl-lysogangliosides and physiologically acceptable salts thereof, especially those of formula (I):

wherein (Abstract continued on next page.)

ABSTRACT

R represents —CH=CH(CH$_2$)nCH$_3$ or —CH$_2$CH$_2$(CH$_2$)nCH$_3$;

n is 12 or 14;

R$^1$ represents

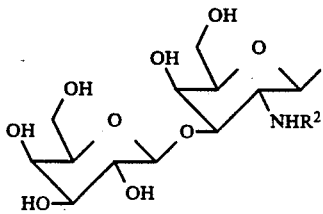

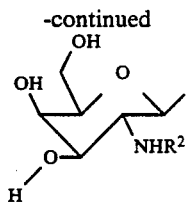

or hydrogen; and

R$^2$ represents hydrogen or acetyl; for use in therapy.

The compounds are useful as inhibitors of phospholipases A$_2$, and of superoxide production, as antiproliferative and immunosuppressant agents in the treatment of autoimmune diseases. The invention also relates to the use of N-deacetyl-lysogangliosides for the manufacture of medicaments for the treatment of the aforementioned conditions.

3 Claims, 19 Drawing Sheets

EFFECT OF MONO-N-DEACETYL-LYSO-$GM_1$ ($GM_1L$) AND INTERFERONS ON LEUKEMIA L1210 PROLIFERATION

48 HOURS

72 HOURS

L1210 CELLS × ($10^3$)

EFFECT OF MONO-N-DEACETYL-LYSO-$GM_1$ ($GM_1L$) AND INTERFERONS ON DAUDI CELLS PROLIFERATION

48 HOURS

72 HOURS

DAUDI CELLS × ($10^3$)

EFFECT OF PREINCUBATION OF LEWIS LUNG CARCINOMA CELLS WITH MONO-N-DEACETYL-LYSO-$GM_1$ ($GM_1L$) ON THEIR ONCOGENICITY

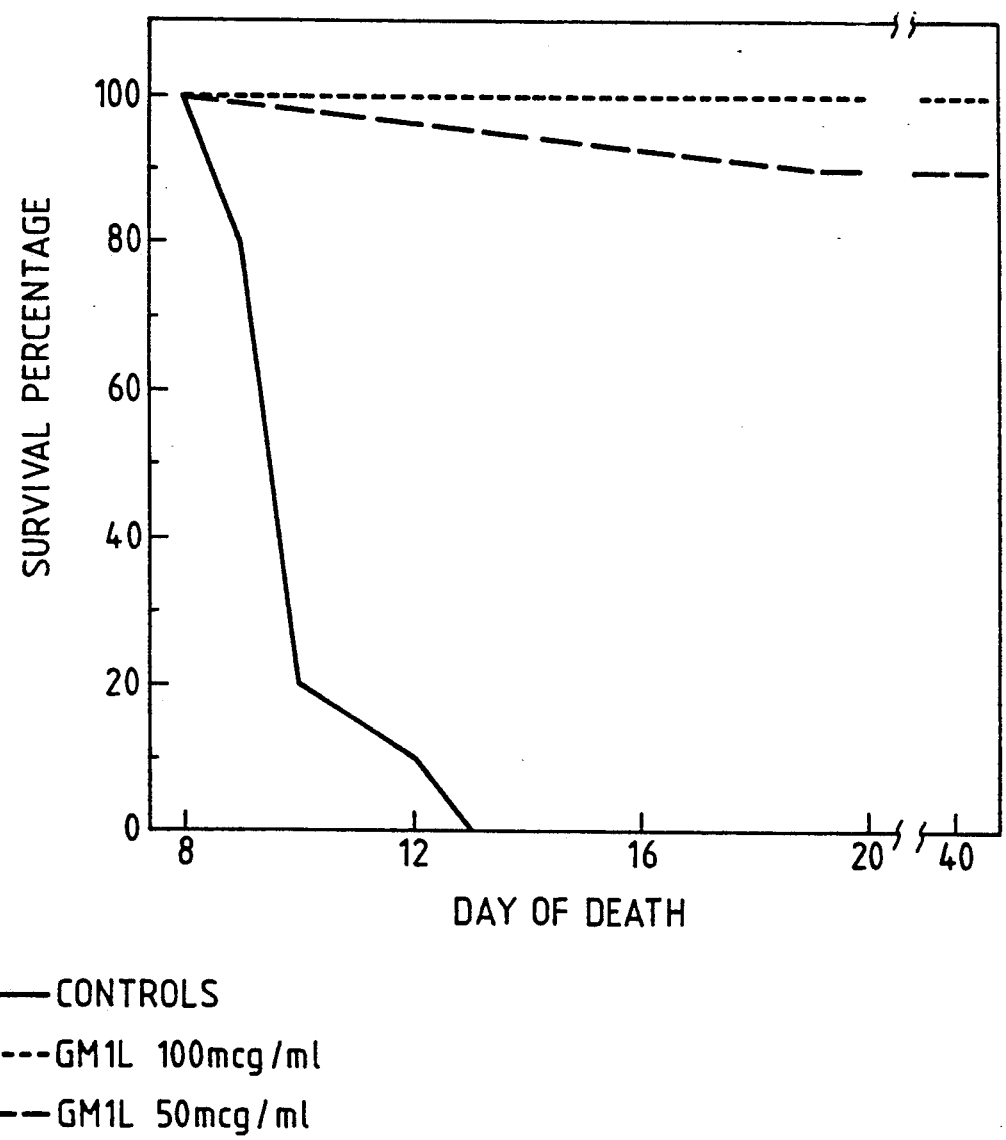

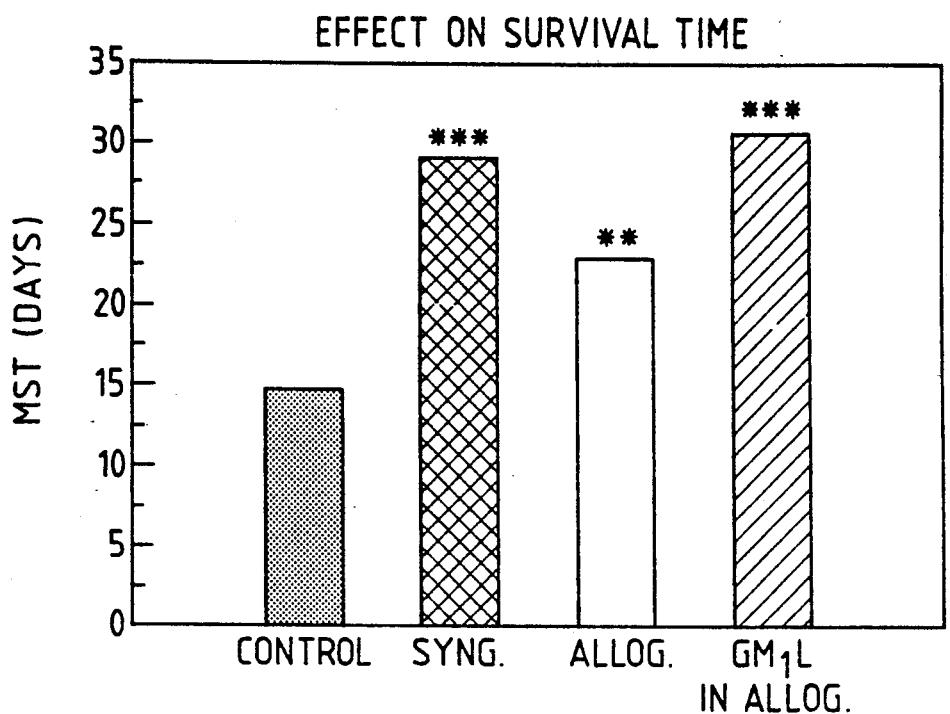
Fig. 12. BONE MARROW GRAFT REJECTION EFFECT OF MONO-N-DEACETYL-LYSO-$GM_1$ ($GM_1L$)
EFFECT ON SURVIVAL TIME
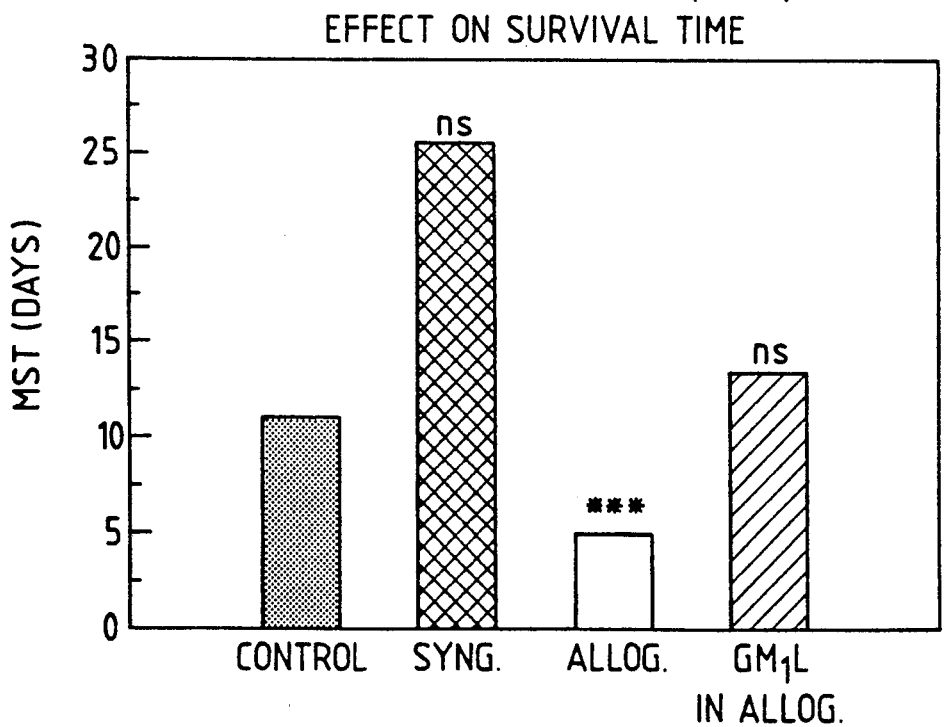
Fig. 13. BONE MARROW GRAFT REJECTION EFFECT OF MONO-N-DEACETYL-LYSO-$GM_1$ ($GM_1L$)
EFFECT ON SURVIVAL TIME EFFECT OF MONO-N-DEACETYL-LYSO-$GM_1$ ($GM_1L$) TREATMENT ON MORTALITY DUE TO EAE INDUCTION WITH BOVINE MYELIN IN GUINEA PIGS PROTECTIVE EFFECT OF MONO-N-DEACETYL-LYSO-$GM_1$ ($GM_1L$) ON GUINEA PIGS AFTER EAE INDUCTION (BY BOVINE MYELIN)

CLINICAL SCORES AND CRITERIA FOR RELAPSE:
0 - NO SIGNS; 1 - WEIGHT LOSS; 2 - MILD PARESIS; 3 - MODERATE PARESIS; 4 - SEVERE PARESIS, AND FAECAL IMPACTION; 5 - DEATH

EFFECT OF DI-N-DEACETYL-LYSO-$GM_1$-$C_{20}$ ON HOG PANCREAS $PLA_2$ ON LIPOSOMES

EFFECT OF DI-N-DEACETYL-LYSO-$GM_1$-$C_{20}$ ON RABBIT PLATELET AGGREGATION <u>IN VIVO</u>

A.A. 3mcl = 45mcg/ml
TIME 0

A.A. 3mcl = 45mcg/ml
>18hrs

DI-N-DEACETYL-LYSO-$GM_1$-$C_{20}$ AT 0.2mg/kg p.o.
A.A. = ARACHIDONIC ACID

EFFECT OF DI-N-DEACETYL-LYSO-GM$_1$-C$_{20}$ ON RABBIT PLATELET AGGREGATION IN VIVO

DI-N-DEACETYL-LYSO-GM$_1$-C$_{20}$ AT 0.13mg/kg p.o.
A.A. = ARACHIDONIC ACID

EFFECT OF DI-N-DEACETYL-LYSO-$GM_1$-$C_{20}$ ON THROMBIN-INDUCED THROMBOEMBOLISM IN MICE

DI-N-DEACETYL-LYSOGANGLIOSIDES

The present invention relates to ganglioside derivatives, their use as therapeutic agents, methods for the preparation of said derivatives, and pharmaceutical compounds containing them. In particular this invention relates to N-deacylated derivatives of monosialogangliosides useful as inhibitors of phospholipases $A_2$, and of superoxide production, as antiproliferative and immunosuppressant agents and in the treatment of autoimmune diseases

BACKGROUND OF THE INVENTION

The gangliosides are a class of naturally occurring glycosphingolipids comprising an oligosaccharide moiety to which may be attached one or more sialic acid groups, and a ceramide portion which contains a sphingosine or sphinganine chain and an acyl moiety derived from a fatty acid. Gangliosides have been found in the brain, spleen, liver, kidneys and blood of mammals and also in chicken eggs (see Ledeen, *J. Supramolecular Structure*, 8:1-17 (1978) Cell Surface Carbohydrates and Biological Recognition 437-453 for a general review of the gangliosides).

According to the nomenclature proposed by Svennerholm (*J. Neurochem.*, 10, 613, 1963) the various gangliosides are designated by the letter G followed by one of four letters, M, D, T or Q depending on whether the ganglioside is a mono-, di-, tri or tetra-sialo-ganglioside. Thus for example the ganglioside $GM_1$ is a monosialoganglioside with the following structure:

that derived from stearic acid ($C_{18}$) being the major component; other fatty acyl components include those derived from myristic ($C_{14}$) arachidic ($C_{20}$) and lignoceric ($C_{24}$) acids. (Sonnino et al., Journal of Lipid Research, Vol 26, 1985 p248; and Gazzotti et al., Journal of Neuroscience Research 12:179-192, 1984). $GM_2$ has a similar structure but lacks the galactose moiety (IV) of the above structure and $GM_3$ lacks both the galactose and N-acetyl-galactosamine (III) moieties. The numbering of the hexopyranoside moieties (I) to (IV) and the designation of the sialic acid group (A) are the designations proposed by Sillerud et al., *Biochemistry* 1982, 21, 1260-1271, and Koerner et al., *Biochemistry 1983, 22, 2676-2687* and will be followed hereinafter.

A closely related class of sphingolipids is the lysosphingolipids, also known as lysogangliosides, which lack the fatty acyl moiety of the corresponding ganglioside. It has been reported that lysogangliosides are potent inhibitors of protein kinase C activity and phorboldiester binding, suggesting they have a role in neurological disorders (Hannun and Bell, Science Vol 235 p670-674). Neuenhofer et al, *Biochemistry*, (1985) 24 p525-532, describes the synthesis of various lysogangliosides by deacylation of gangliosides $GM_{21}$, $GM_1$ and $GD_{1a}$, to remove both the fatty acyl moiety and the acetyl group present on the sialic acid residue, followed by reacylation of the sialic acid. The paper also indicates that traces of the completely deacylated $GM_1$ and $GD_{1a}$ were revealed by FAB mass analysis. No biological activity is ascribed to these compounds.

Sonnino et al. (Journal of Lipid Research, Vol 26, 1985 p248) describe the preparation of various deriva-

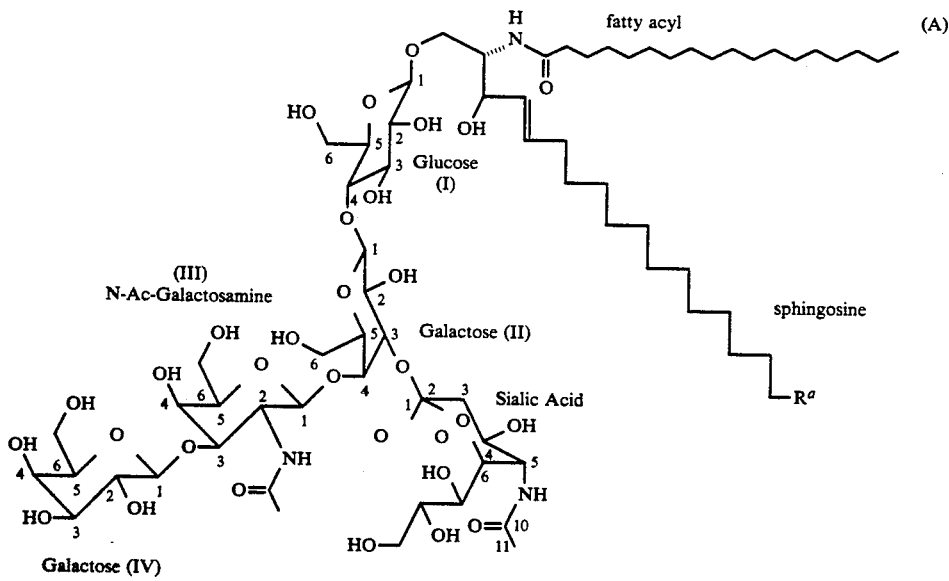

wherein $R^a$ is $-CH_3$ or $-C_3H_7$. $GM_1$ isolated from natural sources is generally a mixture of molecules wherein $R^a$ is $-CH_3$ and those wherein $R^a$ is $-C_3H_7$ that is having a carbon chain length of 18 or 20 C-atoms. It will be appreciated that the molecule may be in the erythro or threo configuration with respect to the double bond in the sphingosine chain, but the naturally occurring form is the erythro configuration. Naturally occurring $GM_1$ also contains a small proportion of molecules having a fully saturated sphinganine chain in place of the sphingosine moiety. In addition there is some variation in the length of the fatty acyl chain, with tives of $GM_1$ in which the naturally occurring fatty acyl moiety is replaced with a different fatty acyl moiety. The synthesis of these compounds also proceeds via the lysoganglioside derivative of $GM_1$ in which the sialic acid moiety is deacetylated. No biological activity is ascribed to these compounds.

In this specification lysoganglioside derivatives in which the sialic acid residue only is deacetylated will be referred to as mono-N-deacetyl-lysogangliosides e.g. mono-N-deacetyl-lyso-$GM_1$ and lysogangliosides in which both the sialic acid and N-galactosamine residues are deacetylated will be referred to as di-N-deacetyl-lysogangliosides. The expression 'N-deacetyl lysoganglioside' will be used in this specification to mean a mono- or di-N-deacetyl lysoganglioside as well as mixtures thereof. It will be understood that the foregoing terms are not intended to imply any particular route of preparation of these compounds, but they embrace the compounds per se, whether or not they have been prepared by direct deacetylation of the corresponding lysoganglioside $GM_1$.

BRIEF DESCRIPTION OF THE DRAWINGS

The invention is illustrated in the attached drawings in which

FIGS. 10 and 11 are graphs displaying the results of Example 7;

FIGS. 12 and 13 are graphs showing the results of Example 8;

DETAILED DESCRIPTION OF THE INVENTION

Figure 1:
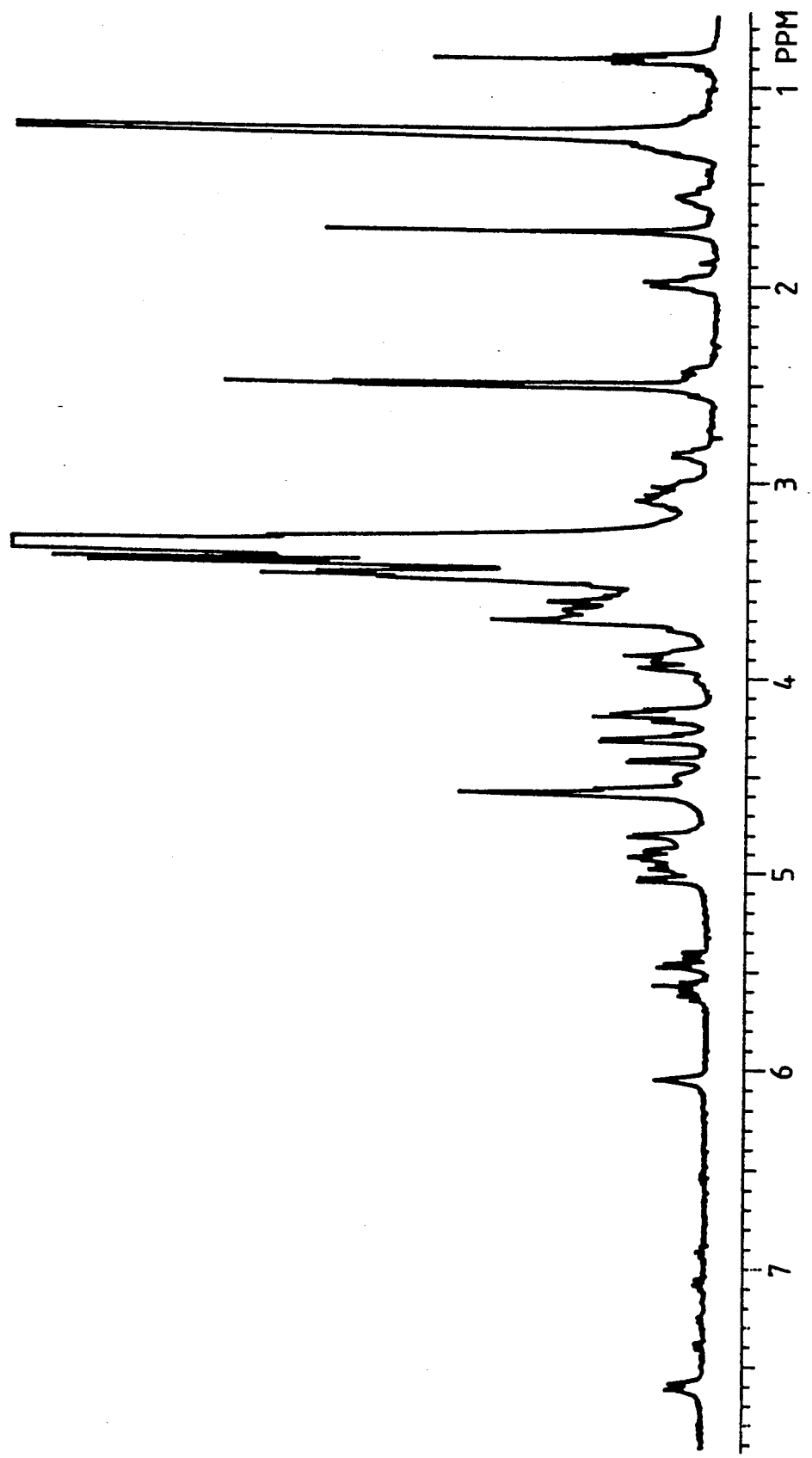
FIGS. 1–7 are $^1H$ nmr spectra of the ganglioside products prepared in Examples 1–4.

It has now been found that certain N-deacetyl-lysogangliosides exhibit therapeutically useful biological activity in a variety of test systems as will be described in more detail hereinafter.

In a first aspect therefore the present invention provides an N-deacetyl lysoganglioside or physiologically acceptable salt thereof for use as a medicament, that is, for use in therapy. Said N-deacetyl-lysoganglioside preferably corresponds to a ganglioside $GM_1$, $GM_2$, $GM_3$ or $GD_{1a}$.

Preferred derivatives for use according to the invention are those of formula (I):

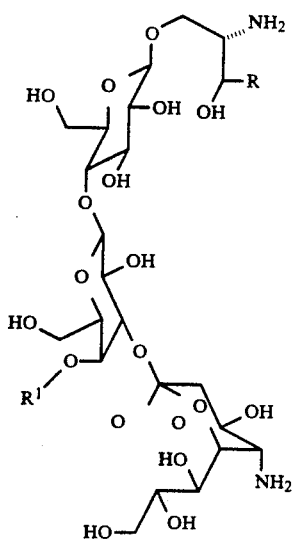

wherein

R represents $-CH=CH(CH_2)nCH_3$ or $-CH_2CH_2(CH_2)nCH_3$;

n is 12 or 14;

$R^1$ represents

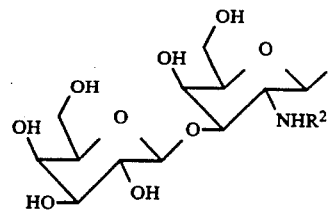

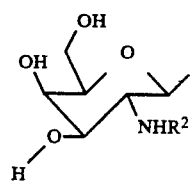

or hydrogen; and $R^2$ represents hydrogen or acetyl;

and physiologically acceptable salts thereof.

Preferred compounds for use according to the present invention include mono-N-deacetyl-lyso-$GM_1$ and di-N-deacetyl-lyso $GM_1$ i.e. the compounds of formula (I) wherein $R^1$ represents

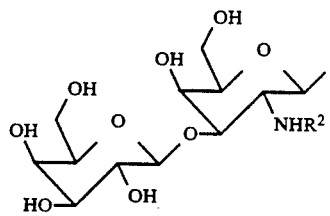

and $R^2$ represents respectively acetyl or a hydrogen atom.

Preferably $R^2$ represents hydrogen.

Further preferred compounds are those of formula (I) wherein n is 14 i.e. those having a $C_{20}$ sphingosine or sphinganine chain. A particularly preferred compound of the present invention is the compound of formula (I) wherein R represents $-CH=CH(CH_2)nCH_3$ or $-CH_2CH_2(CH_2)nCH_3$, n is 14, $R^1$ is a residue

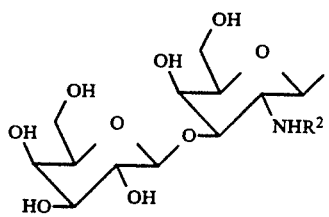

and $R^2$ is a hydrogen atom, which compound is herein designated: di-N-deacetyl-lyso-$GM_1$-$C_{20}$.

Preferably R represents $-CH=CH(CH_2)nCH_3$.

Di-N-deacetyl-lyso-$GM_1$ i-$C_{20}$ is believed to be a novel compound and as such forms a further aspect of the present invention.

Further novel compounds according to the present invention are the corresponding compound wherein n represents 12, and the corresponding monodeacetyl lysogangliosides, herein respectively designated:
di-N-deacetyl-lyso-$GM_1$-$C_{18}$;
mono-N-deacetyl-lyso-$GM_1$-$C_{20}$; and
mono-N-deacetyl-lyso-$GM_1$-$C_{18}$.

Salts of the N-deacetyl lysogangliosides include salts formed with acids and salts formed with bases, and are preferably physiologically acceptable. Suitable acid addition salts include those formed from hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic and glucuronic acids. Suitable base salts include inorganic base salts such as alkali metal (e.g. sodium and potassium) salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine salts.

N-deacetyl-lysogangliosides for use according to the present invention have been found to inhibit phospholipases $A_2$ ($PLA_2$), enzymes, both in vitro and in vivo. $PLA_2$ catalyses the release of arachidonic acid from cell membranes, which acid is then converted in the body to prostaglandins, leukotrienes and thromboxanes. $PLA_2$ is also involved in generation of platelet activating factor from alkylacetyl phosphatidyl choline. Thus $PLA_2$ plays a role in a number of conditions including inflammation, thrombotic disorders and allergic disorders. N-deacetyl lysogangliosides have also been found to inhibit superoxide production from human peripheral blood neutrophils in vitro. Superoxide production is believed to be involved in inflammatory processes and reperfusion injury such as occurs in cardiac infarct and kidney ischemia.

N-deacetyl lysogangliosides have also been found to inhibit the proliferation of leukemia L1210 cells and of Daudi cells in vitro, and to decrease the mortality rate in mice implanted with an experimental Sarcoma 180 tumour. Furthermore it has been found that mice challenged with tumour cells which have been pretreated in vitro with an N-deacetyl lysoganglioside have an increased survival time as compared with mice challenged with untreated tumour cells, indicating that N-deacetyl lysogangliosides reduce the oncogenicity of the tumour cells. Mono-N-deacetyl-lyso $GM_1$ has been demonstrated to have an immunosuppressant effect in an experimental bone marrow transplant in irradiated mice. Without treatment, mice given an allogeneic bone marrow transplant (i.e. bone marrow which is not genetically identical) have a lower survival time (indicating rejection of the bone marrow) than mice given a syngeneic transplant (genetically identical bone marrow), whereas treatment with mono-N-deacetyl-lyso $GM_1$ has been found to increase the survival time of mice given an allogeneic transplant, in one instance equal to the survival time for a syngeneic transplant. Additionally, it has been found that mono-N-deacetyl-lyso $GM_1$ exhibits a protective effect on guinea pigs and reduces the mortality rate in the experimental allergic encephalomyelitis test which is a standard animal test model for autoimmune conditions such as multiple sclerosis. (Borel J. F. and Gunn H. C. Annals N.Y. Academy of Science 1986, 475, 307–319).

In a further aspect the present invention provides the use of an N-deacetyl lysoganglioside in the manufacture of a medicament for the treatment of conditions requiring inhibition of phospholipases $A_2$ or the inhibition of superoxide production, the treatment of a proliferative or autoimmune disease, or suppression of the immune system.

Conditions requiring inhibition of phospholipases $A_2$ include inflammation for example chronic inflammatory diseases such as arthritis, and inflammatory bowel disease; asthma; and thrombotic disorders for example the prevention of coronary disease or for treatment after an initial heart attack, to prevent subsequent attacks.

Conditions requiring inhibition of superoxide production include reperfusion injury for example in cardiac infarct and kidney ischemia. Proliferative diseases include various forms of cancer, including leukemias, lymphomas, sarcomas and solid tumours; basal and squamous cell carcinomas of the skin; and psoriasis.

Conditions requiring suppression of the immune system include for example preventing rejection of transplanted organs, including heart, liver, kidneys, bone marrow and endocrine glands. Autoimmune diseases, which are characterised by altered immunological reactivity and manifestations of autoimmunity, include collagen-vascular disorders, such as systemic lupus erythematosus (SLE), necrotising vasculitis, scleroderma, polymyositis, and rheumatoid arthritis; regional enteritis; ulcerative colitis; chronic active hepatitis; glomerulonephritis; Goodpasture's syndrome; autoimmune hemolytic anaemia; idiopathic thrombocytopenic purpura; pemphigus vulgaris; pemphigoid; primary myxoedema; Hashimoto's thyroiditis; thyrotoxicosis; pernicious anaemia; autoimmune atrophic gastritis; Addison's disease; juvenile diabetes; myasthenia gravis; sympathetic ophthalmia; phacogenic uveitis; multiple sclerosis; ideopathic leucopenia; primary binary cirrhosis; Sjogren's syndrome; dermatomyositis and discoid LE.

The amount of N-deacetyl lysoganglioside required to be effective as a medicament will, of course, vary and is ultimately at the discretion of the medical or veterinary practitioner. The factors to be considered include the condition being treated, the route of administration, and nature of the formulation, the mammal's body weight, age and general condition, and the particular compound to be administered. A suitable therapeutic dose is in the range of about 0.0005 to about 10 mg/kg bodyweight, e.g. 0.01 to about 5 mg/kg body weight, preferably in the range of about 0.1 to 2 mg/kg. The total daily dose may be given as a single dose, multiple doses, eq., two to six times per day or by intravenous infusion for selected duration. For example, for a 75 kg mammal, the dose range for would be about 0.5 to 500 mg per day e.g. 10 to 250 mg per day, and a typical dose could be about 100 mg per day. If discrete multiple doses are indicated treatment might typically be 25 mg of a compound of formula (1) given up to 4 times per day. A suitable effective dose for anti-tumour treatment is in the range of about 0.1 to about 10 mg/kg bodyweight e.g. 1 to 5 mg/kg. For anti-tumour treatment a suitable dose range for a 75 kg mammal is 10 to 750 mg per day, e.g. 50 to 500 mg per day.

Whilst it is possible for an N-deacetyl lysoganglioside according to the invention to be administered alone, it is preferable to present said compound in a pharmaceutical formulation. Formulations of the present invention for medical use comprise an N-deacetyl lysoganglioside or a physiologically acceptable salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising an N-deacetyl lysoganglioside or a physiologically acceptable salt thereof together with a pharmaceutically acceptable carrier therefor.

There is also provided a method for the preparation of a pharmaceutical formulation comprising bringing into association an N-deacetyl lysoganglioside or a physiologically acceptable salt thereof, and a pharmaceutically acceptable carrier therefor.

Formulations according to the present invention include those suitable for oral, topical, rectal or parenteral (including subcutaneous, intramuscular and intravenous) administration. Preferred formulations are those suitable for oral or parenteral administration. For treatment of solid tumours an N-deacetyl lysoganglioside may also be formulated for percutaneous administration around the perimeter of the tumour.

The formulations may conveniently be presented in unit dosage form and may be prepared by any of the methods well known in the art of pharmacy. All methods include the step of bringing the N-deacetyl lysoganglioside into association with a carrier which constitutes one or more accessory ingredients. In general, the formulations are prepared by uniformly and intimately bringing said compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the N-deacetyl lysoganglioside; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the N-deacetyl lysoganglioside in a free-flowing form such as a powder or granules, optionally mixed with a binder, lubricant, inert diluent, surface active or dispersing agent. Moulded tablets may be made by moulding in a suitable machine a mixture of the powdered compound with any suitable carrier.

A syrup may be made by adding the N-deacetyl lysoganglioside to a concentrated, aqueous solution of a sugar, for example sucrose, to which may also be added any accessory ingredients. Such accessory ingredient(s) may include flavourings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the N-deacetyl lysoganglioside which is preferably isotonic with the blood of the recipient.

Useful formulations also comprise concentrated solutions or solids containing an N-deacetyl lysoganglioside which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

The N-deacetyl lysogangliosides for use according to the present invention may be administered in combination with other therapeutic agents, for example in a combined pharmaceutical formulation, or concurrently with other agents as part of the same treatment regimen. Such other therapeutic agents include for example other immunosuppressants such as cyclophosphamide; antitumour agents; corticosteroids; cytokines; non-steroidal anti-inflammatory agents; antihistamine agents; antiserotonin agents and antiplatelet agents.

The N-deacetyl-lysogangliosides for use according to the present invention may be prepared from a sialoganglioside by subjecting said sialoganglioside to alkaline hydrolysis in a suitable solvent, for example an alcohol such as a $C_{1-4}$ alkanol, and at an elevated temperature, conveniently in the range 100°–130° C., or by using enzymatic hydrolysis. The alkaline hydrolysis may be effected by methods well known in the art, conveniently using aqueous sodium or potassium hydroxide or tetramethylammonium hydroxide in admixture with a $C_{1-4}$ alkanol, e.g. methanol or n-butanol. The hydrolysis may be conveniently carried out at reflux temperature. The duration of hydrolysis will depend on the other conditions used, but in general will be at least 3 hours and may continue for up to 30 hours. As will be readily apparent to those skilled in the art, the level of deacylation achieved will depend upon the precise combination of reaction conditions used and if a complete deacylation is required, to produce a di-N-deacetyl-lysoganglioside, more stringent conditions should be chosen than are used to effect a partial de-acylation of the starting material. It will also be appreciated that the reaction can be monitored for example by thin layer chromatography or by spectroscopic analysis of the reaction mixture, and the end point thus determined. The N-deacetyl lysoganglioside may subsequently be obtained from the reaction mixture by methods well-known in the art e.g. by removing the organic solvent and dialysis against water, conveniently for a period between 24 and 72 hours, preferably 48 hours. Either distilled or natural water may be used in this step. The resulting solution may be freeze-dried or subjected to further purification, e.g. by column chromatography. If the product contains a mixture of mono- and di-N-deacetyl lysogangliosides these may be separated by column chromatography.

Sialogangliosides which may be employed as starting materials in the above process are preferably monosialogangliosides and include $GM_1$, $GM_2$, $GM_3$ and $GD_{1a}$. It will be appreciated that the nature of the fatty acyl moiety in the starting material is not of importance, as this moiety is not present in the final product. Preferably the ganglioside starting material is in the naturally-occuring erythro form.

The N-deacetyl lysoganglioside derivatives obtainable according to the above process will usually contain less than 50%, preferably less than 30% and most preferably less than 10% of impurities, such as the ganglioside starting material and other ganglioside derivatives. Purification of the N-deacetyl lysoganglioside initially obtained may be effected by methods well known in the art, such as column chromatography.

In a further aspect of the invention there is provided a mono- or di-N-deacetyl lysoganglioside $GM_1$ characterised in that it is at least 50%, preferably at least 70% e.g. at least 90% pure.

It will be appreciated that where the starting material comprises a mixture of homologous compounds, such as $GM_1$ or $GD_{1a}$ which each exists as a mixture of the compound wherein n is 12 and wherein n is 14, the corresponding N-deacetyl lysoganglioside may also be a mixture of homologues. The purity of the final compound is calculated with reference to such mixtures, and not to any one homologue. The ratio of homologues obtained in the preparation of the N-deacetyl lysogangliosides may vary within wide limits. In practice however it is found to be close to a 1:1 mixture. Similarly, where a proportion of the starting ganglioside is in the sphinganine form the final compound will also contain a proportion of sphinganine moieties.

An N-deacetyl lysoganglioside containing both $C_{18}$ and $C_{20}$ components, (i.e. a mixture of compounds wherein n is 12 and 14) can be separated by chromatographic methods to give the individual $C_{18}$ and $C_{20}$ components. Alternatively, the ganglioside starting material, such as $GM_1$ may first be separated for example by chromatographic methods, into its $C_{18}$ and $C_{20}$ components, which can then be used to prepare the corresponding $C_{18}$ and $C_{20}$ N-deacetyl lysogangliosides according to the general method described hereinabove. The $C_{18}$ component of the starting ganglioside is preferably eluted using an aqueous organic solvent and the $C_{20}$ component is preferably eluted with a non-aqueous organic solvent.

The $C_{18}$ and $C_{20}$ N-deacetyl lysoganglioside derivatives obtainable according to the above processes will usually contain less than 50%, preferably less than 30% and most preferably less than 10% of impurities such as ganglioside starting material or other ganglioside derivatives. In a further aspect of the invention there is provided a $C_{18}$ or $C_{20}$ mono- or di- N-deacetyl lysoganglioside characterised in that it is in substantially pure form, for example at least 50%, preferably at least 70% e.g. at least 90% pure. Preferably the said $C_{18}$ or $C_{20}$ N-deacetyl lysoganglioside is selected from mono-N-deacetyl-lyso $GM_1$-$C_{20}$
mono-N-deacetyl-lyso $GM_1$-$C_{18}$
di-N-deacetyl-lyso $GM_1$-$C_{20}$
di-N-deacetyl-lyso $GM_1$-$C_{18}$ in substantially pure form.

DESCRIPTION OF THE PREFERRED EMBODIMENTS

The invention will now be illustrated by the following non-limiting examples:

EXAMPLE 1

Preparation of Mono-N-deacetyl-lyso $GM_1$ and di-N-deacetyl-lyso GM 150 mg of $GM_1$ (Opocrin, purity 98% by HPLC and t.l.c.) were hydrolyzed by refluxing at 115°–117° C. for 3.5 hours with 10ml of a mixture of 10M KOH and butan-1-ol(1/9 v/v). After cooling at room temperature overnight, 10 ml of water were added to the hydrolysis solution and the carefully mixed solution was placed in a separation funnel overnight. The lower water phase which contained lysoganglioside was isolated, concentrated under vacuum to eliminate butanol traces, then adjusted to pH9 with HCl(12N) and clarified by centrifugation (3000 rpm) for 15 minutes. The clear surnatant was dialysed in a Visking tube against 10 l of distilled water (changed 3 times per day) for two days then freeze-dried, to give the hydrolysis product. This was purified by column chromatography on silica gel Si60 (Merck art.9385), using the following mobile phase scheme:

Eluant A: Butan-1-ol/methanol/water (2:2:0.75 v/v/v) 1200 m]
Eluant B: Butan-1-ol/methanol/water (2:2:1 v/v/v) 500 ml 1 g of the hydrolysis product was dissolved in 60 ml of eluant A and sonicated at 45° C. for 60 minutes, followed by filtration through glass wool to eliminate residual insoluble matter. The solution was then chromatographed at a flow rate of 20 ml/min and at 45° C. (water jacket). 50 ml fractions of each eluant were collected and concentrated under vacuum at 400° C..

Fractions from eluant A gave mono-N-deacetyl-lyso GM 1 as a white fluffy powder. Fractions from eluant B gave di-N-deacetyl-lyso $GM_1$ as a white fluffy powder.

Physical Characteristics mono-N-deacetyl-lyso $GM_1$

Rf=0.13 (Plates: Kieselgel 60 TLC F254 (Merck art. 5715)20×20 cm–0.25 mm, activated by heating at 100° C. for 30 minutes and cooled to room temperature just before use. After 1 hour of saturation the plates were developed with chloroform:methanol:2.5M ammonia (50:40:10), as eluant. Detection: 1) Resorcinol, 2) Orcinol).

Preparation of Orcinol Spray:

Solution A: dissolve 1 g iron chloride in 100 ml 10% sulphuric acid.
Solution B: 6% ethanolic orcinol solution.
Mix 10 ml A and 1 ml B immediately before use. After spraying, the plates are heated for 20–25 minutes at 100° C.
Loading: 2011.
Run length: 12.5 cm.

Preparation of Resorcinol Spray:

2 g of resorcinol was dissolved in 100 ml of distilled water. 10 ml of this solution was added to 80 ml of concentrated hydrochloric acid containing 0.25 ml of 0.1M copper sulphate. The volume of the reagent was made up to 100 ml of distilled water. The reagent was prepared at least 4 hours before use.

The $^1H$ nmr spectrum obtained the product was substantially identical to that shown in FIG. 1.

Di-N-deacetyl-lyso-$GM_1$

Figure 2A:
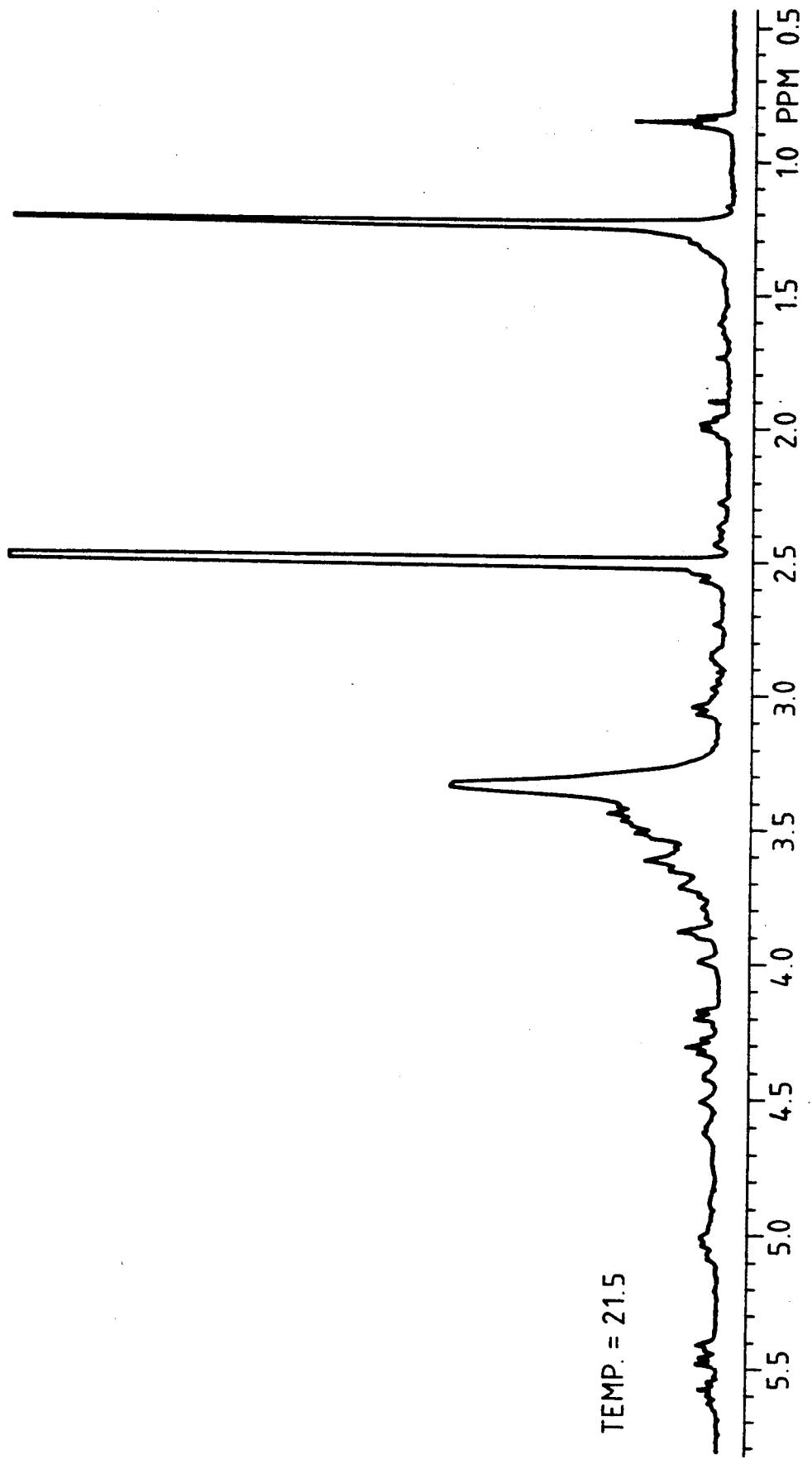
Figure 2B:
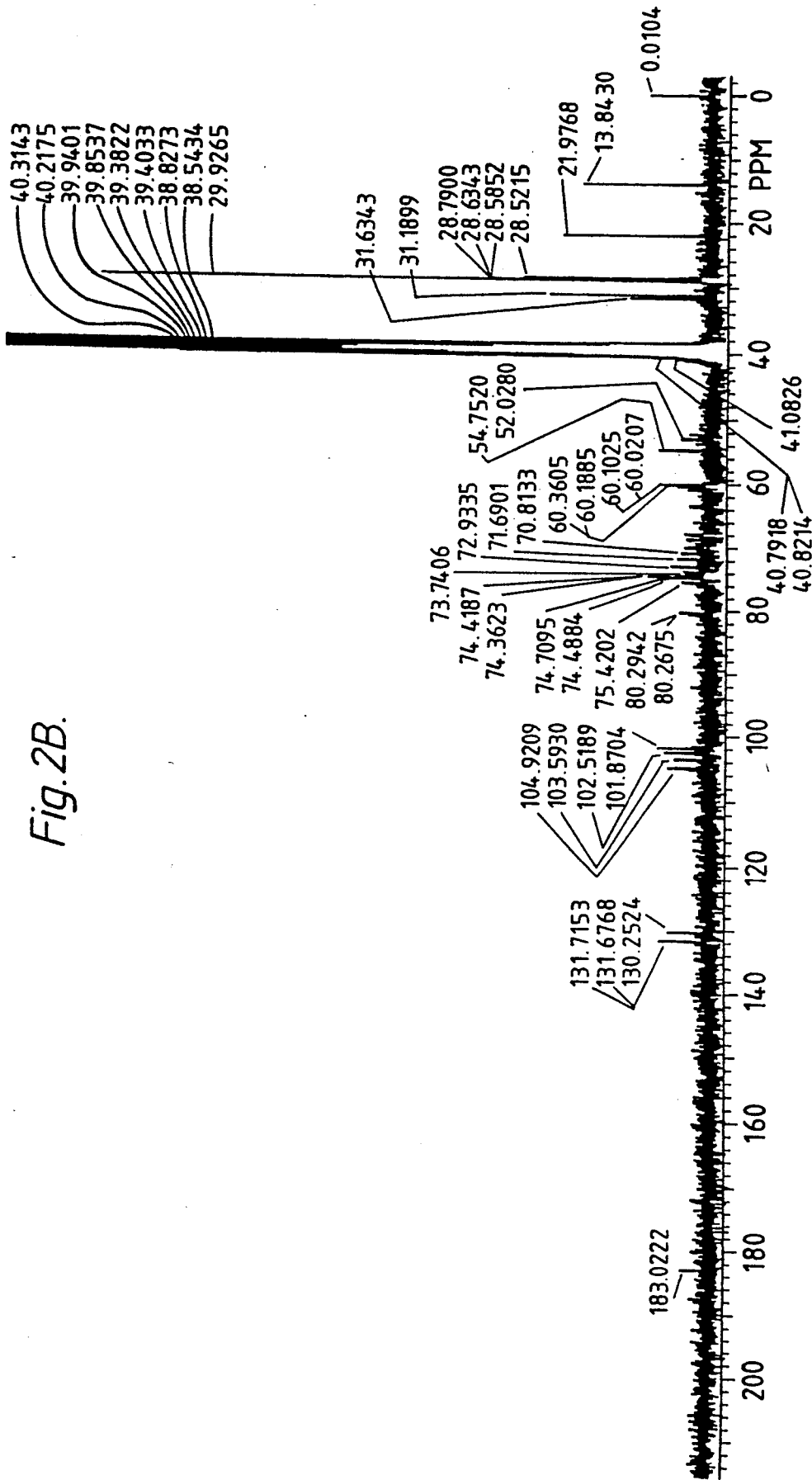

RF=0.05 (Plates and Detection as above) $^1H$ nmr and $^{13}C$ nmr-the spectra obtained were substantially identical to those shown in FIGS. 2(a) and 2(b).

EXAMPLE 2

Preparation of gangliosides $GM_1$-$C_{18}$ and $GM_1$ -$C_{20}$

Eluents

Figure 3:
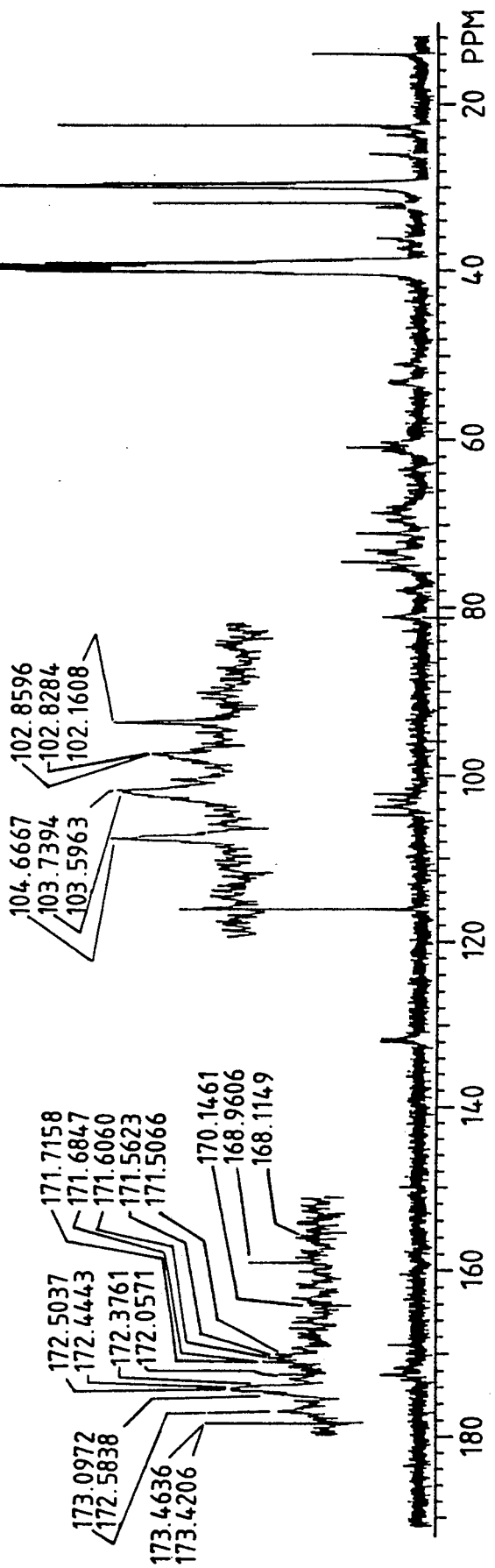
Figure 4:
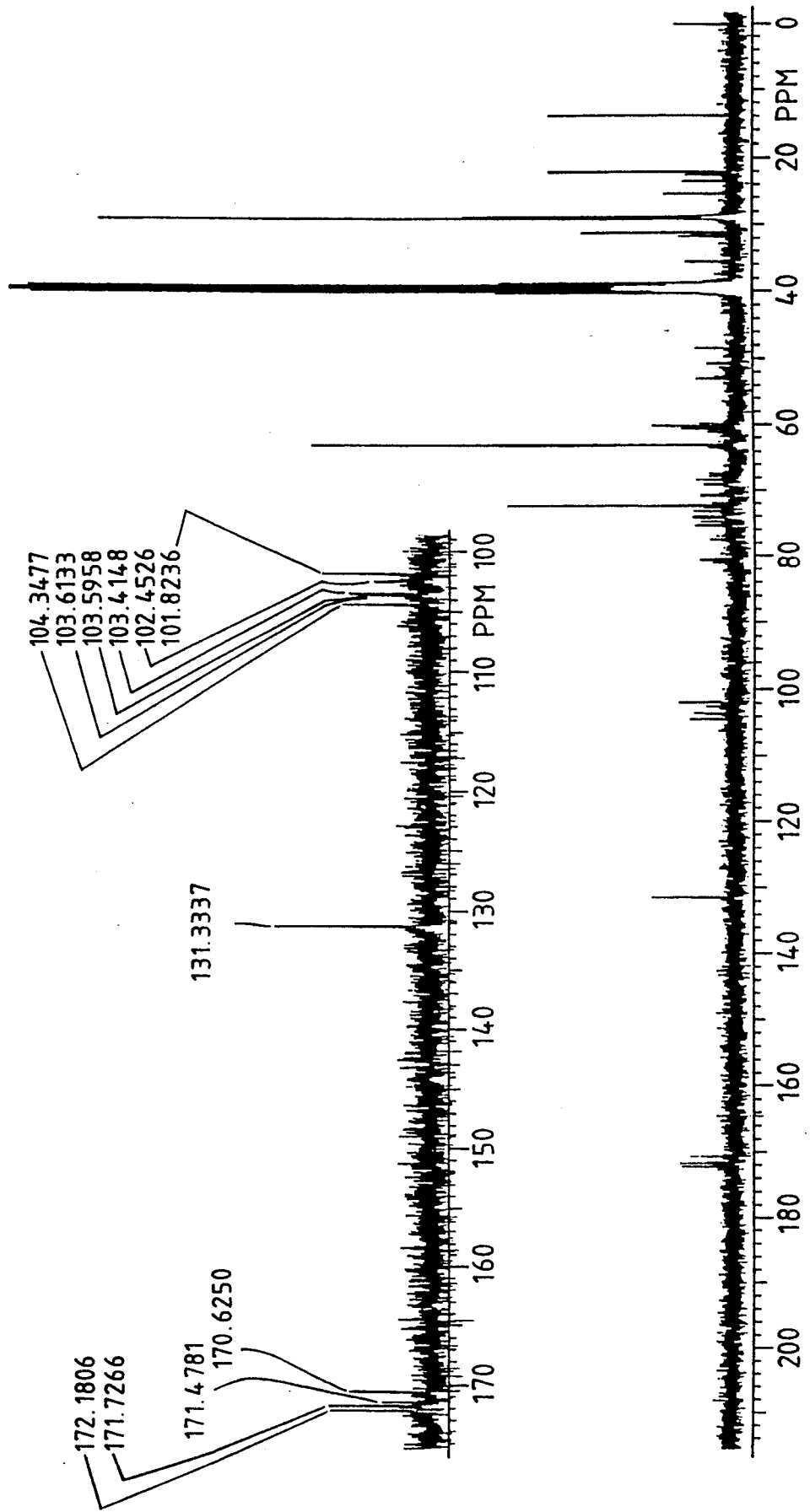

Eluent A:
water:tetrahydrofuran:methanol;16:1:83v/v/v
Eluent B:
water:tetrahydrofuran:methanol;8:8:84v/v/v
Eluent C:
tetrahydrofuran:methanol;10:90v/v 2.5 g. of $GM_1$ (Opocrin) were dissolved in 200 ml of eluent A. The solution was filtered through glass wool to eliminate insoluble material and loaded onto a column (Jobin Yon, diameter 4 cm, height 50 cm) packed with silica (200 g; RP18 25-40]m, art 9303 Merck). The column was eluted successively with Eluent A (3000 ml), Eluent B (800 ml) and Eluent C (800 ml), at a flow rate of 25-30 ml/min and at room temperature. 200 ml fractions of each eluent were collected and concentrated under vacuum at 40° C.. The purity of each fraction was checked by HPLC. Fractions 2-5 gave ganglioside $GM_1$-$C_{18}$ as a powder (50-120 mg/fraction); fractions 6-10 gave a mixture of $GM_1$-$C_{18}$ and $GM_1$-$C_{20}$ as a powder (50-120 mg/fraction); fractions 11-18 gave $GM_1$-$C_{20}$. Values from the $^1H$ nmr spectra obtained on $GM_1$-$C_{20}$ are given in Table 1 below. The 13C nmr spectrum obtained on $GM_1$-$C_{20}$ was substantially identical to that shown in FIG. 3. The 13C spectrum obtained on $GM_1$-$C_{18}$ was substantially identical to that shown in FIG. 4.

EXAMPLE 3 a)

Preparation of di-N-deacetyl-lyso-$GM_1$-$C_{20}$ 3 g. of $GM_1$ $C_{20}$ were hydrolysed by reflux boiling (temperature 118°-121° C.) for 12 hours with 1 L of a mixture of 10M KOH and butan-1-ol [1/9 v/v]. After cooling at room temperature, the reaction mixture was slowly neutralized by several mls of HCl 37until a white precipitate formed, which was allowed to settle for ca. 1 hour. After removal of the upper phase, the precipitate was suspended in 300 mL of distilled water, and reneutralized. Traces of organic solvent were removed under vacuum and the cloudy suspension was dialyzed in a visking tube against 12 L of distilled water (two changes per day for 2 days) and freeze-dried. The freeze dried powder was suspended with 250 mL of distilled water, filtered through a filter paper and washed twice with 100 mL of $H_2O$, to remove any water-insoluble material.

The combined filtrate and washings were filtered through a 0.21 membrane filter and freeze-dried, to give the title compound.

Figure 5:
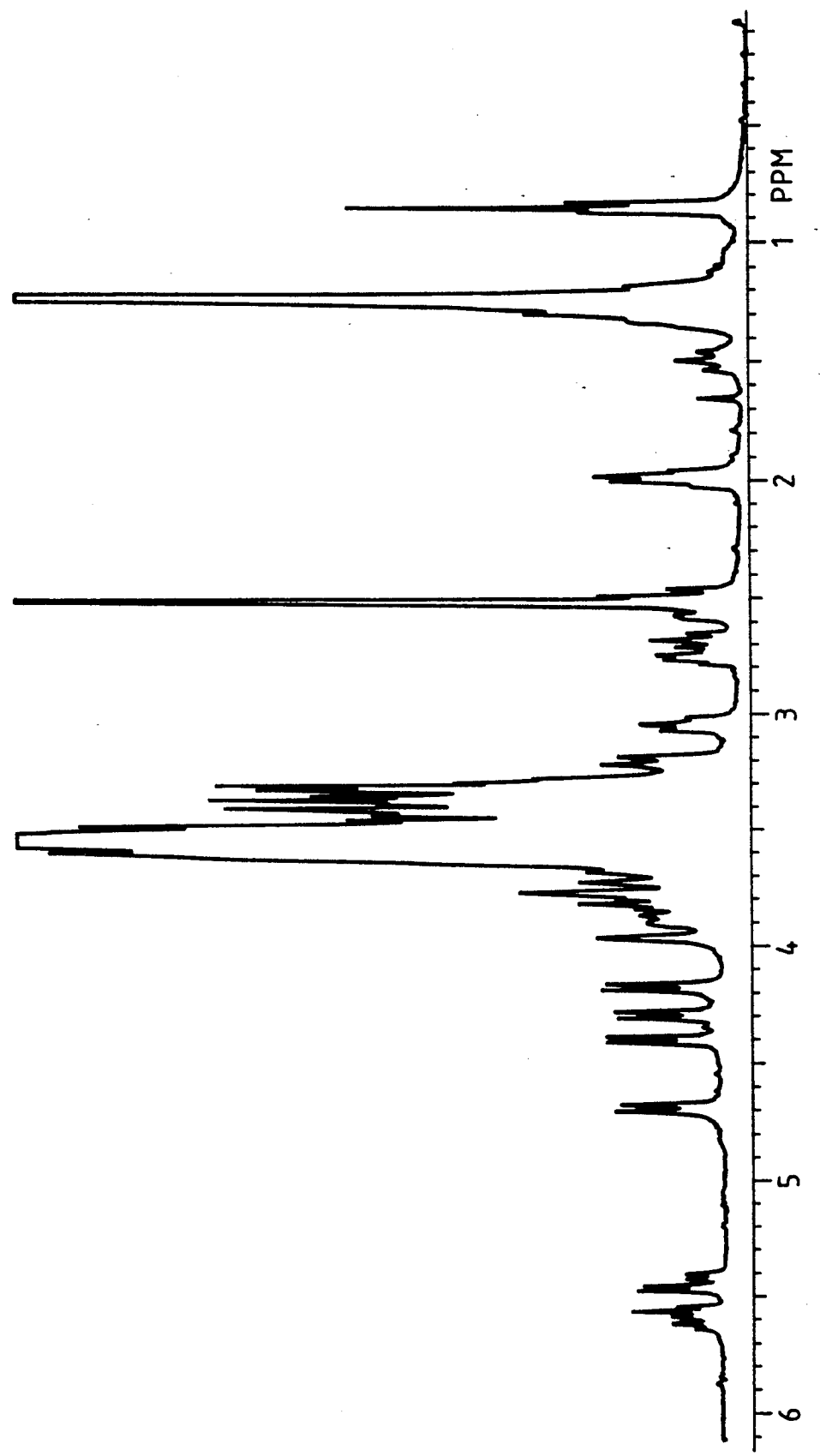

Values from the $^1H$ nmr spectrum obtained on di-N-deacetyl-lyso-$GM_1$-$C_{20}$ are given in Table 1 below. The $^1H$ nmr spectrum is shown in FIG. 5.

b) Preparation of mono-N-deacetyl-lyso-$GM_1$-$C_{20}$ $GM_1$-$C_{20}$ was hydrolysed according to the method of Example 3(a), but the reaction was terminated after 3.50 hours. At this atage the product was found to contain a mixture of mono- and di-N-deacetyl lyso $GM_1$-$C_{20}$, the major component being the monodeacetyl compound. The mixture was separated by column chromatography to give the title compound.

Figure 6:
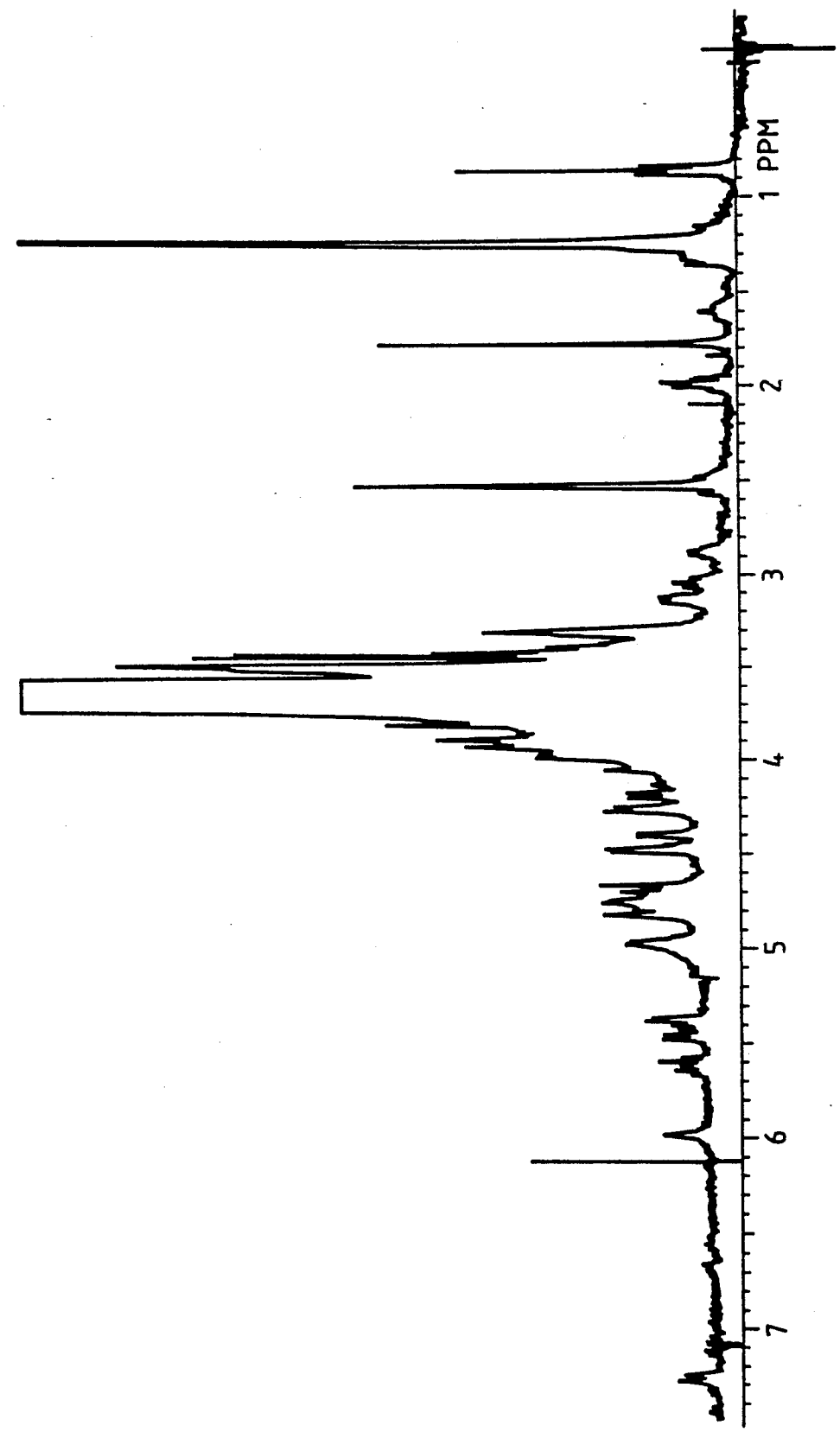

The$^1H$ nmr spectrum is reproduced as FIG. 6.

TABLE 1

|       | Product of Example 2 | Product of Example 3a |
|-------|----------------------|------------------------|
| R4    | 5.34dd; J4, 5=15.1 J3, 4=6.6 | 5.43dd; J4, 5=15.1 J3, 4=6.8 |
| R5    | 5.53dt; J5, 6=7.1    | 5.59dt; J5, 6=6.9      |
| III-1 | 4.82d; J1, 2=8.5     | 4.87d; J1, 2=8.4       |
| II-1  | 4.28d; J1, 2=7.7     | 4.38d; J1, 2=7.7       |
| IV-1  | 4.23d; J1, 2=7.0     | 4.29d; J1, 2=7.3       |
| I-1   | 4.15d; J1, 2=7.8     | 4.18d; J1, 2=7.8       |
| A6    | 3.11d; J=9.6         | 3.12d; J=10.3          |
| A3a   | 1.63t; J3e, 3a=12.4  | 1.54t; J=12.1          |
| R6    | 1.93bs               | 1.98q; J=6.9           |

TABLE 1-continued

|       | Product of Example 2 | Product of Example 3a |
|-------|----------------------|------------------------|
| R8    | 2.02t; J=7.3         | —                      |
| A11   | 1.88s                | —                      |
| III-8 | 1.74s                | —                      |
| R10   | 1.23bs               | 1.23bs                 |
| R14   | 0.85; J=6.9          | 0.85t; J=6.9           |

The numbering in Table 1 follows that proposed by Sillerud et al., *Biochemistry* 1982, 21, 1260-1271 and Koerner et al., *Biochemistry* 1983, 22, 2676-2687 as shown hereinbefore.

EXAMPLE 4 a) Preparation of di-N-deacetyl-lyso-$GM_1$-$C_{18}$

The title compound was prepared in a similar manner to Example 3(a).

b) mono-N-deacetyl-lyso-$GM_1$-$C_{18}$

Figure 7:
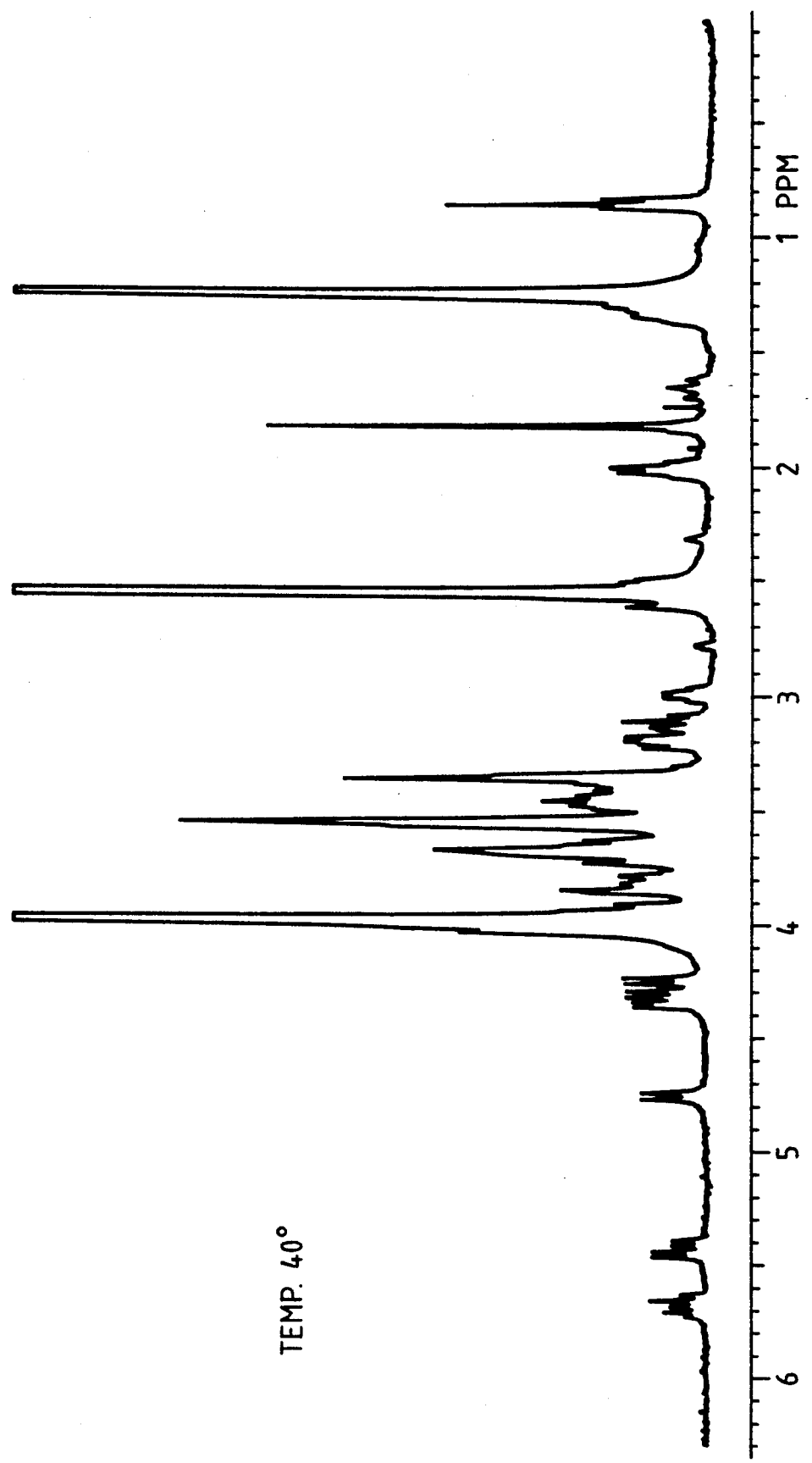
Figure 8A:
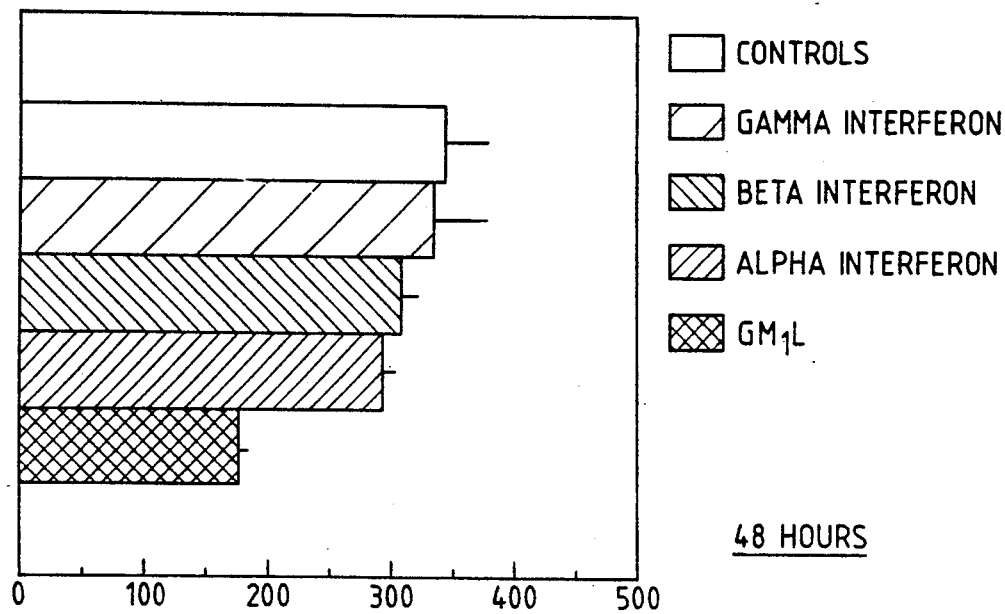
FIGS. 8A, 8B, 9A and 9B are graphs showing the results of Example 5 and the data in Table 2.
Figure 8B:
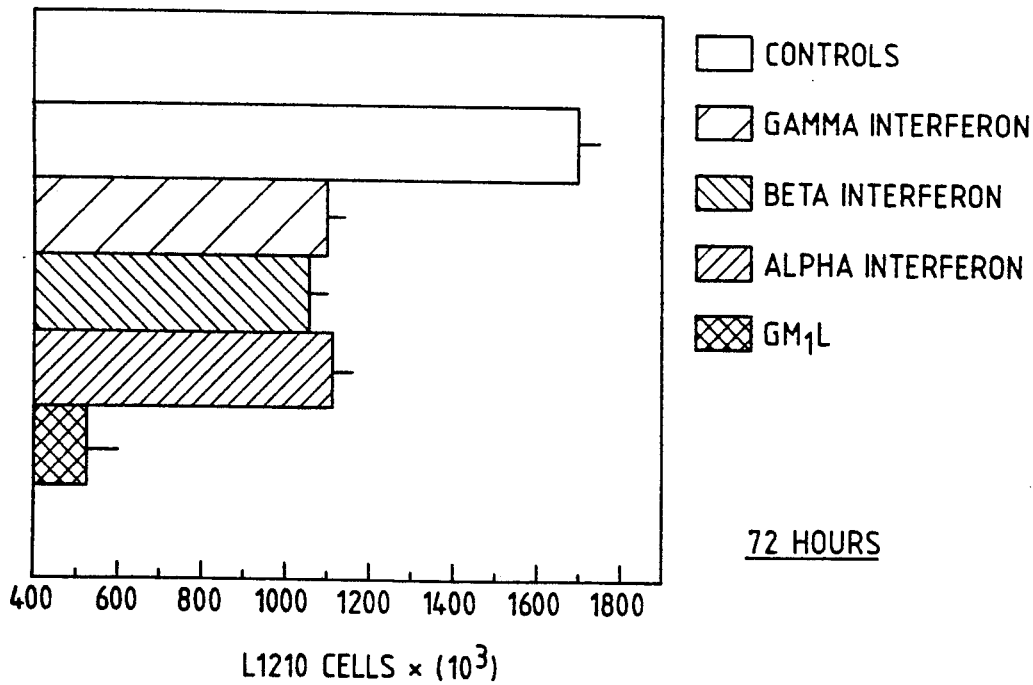
Figure 9A:
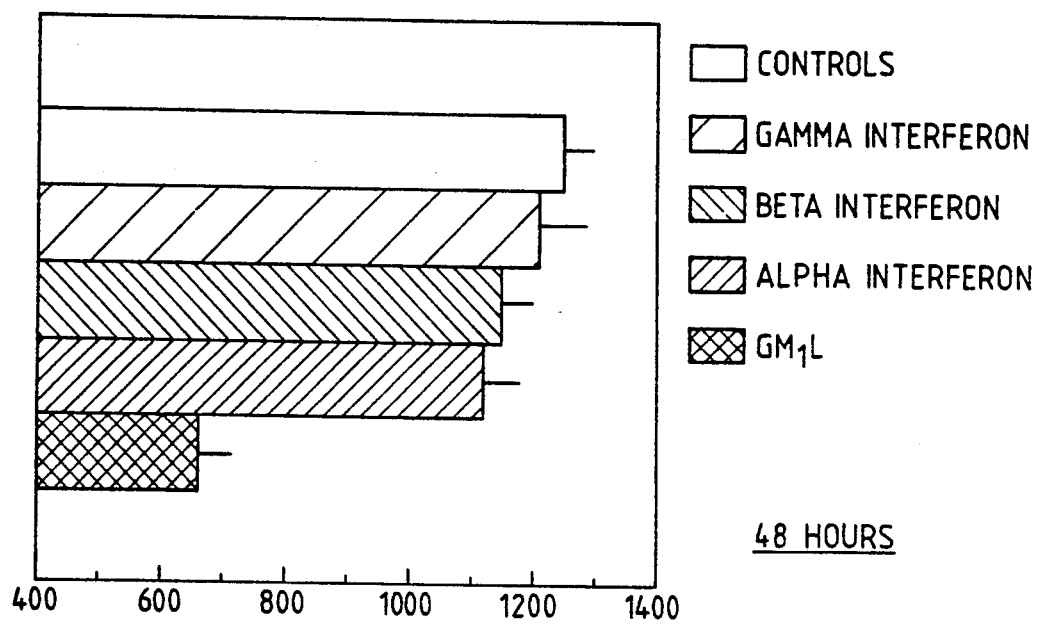
Figure 9B:
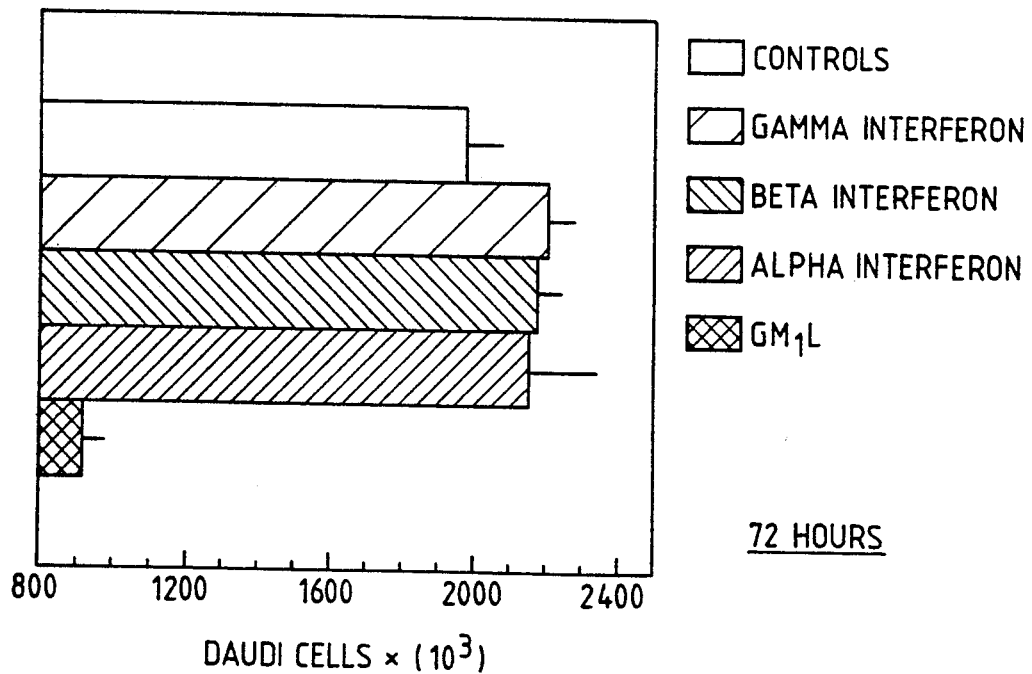

The title compound was prepared using a similar procedure to Example 3(b). The $^1H$ nmr spectrum of the product is reproduced as FIG. 7.

Biological test results

EXAMPLE 5

Effect of mono-N-deacetyl-lyso-$GM_1$ on Proliferation of L1210 and Daudi cells in vitro Method Proliferation assay: The cell lines were maintained in RPMI 1640 medium with 25 mM HEPES buffer and L-Glutamine (GIBCO 041-02400M) supplemented with antibiotics and 10% Foetal Calf Serum Inactivated GIBCO 013-06290H). Tumor cells were washed and diluted with complete medium at the appropriate dilutions and added (2 ml) to wells of FALCON 3047 plate. All drugs in various concentrations, diluted in complete medium, were added to triplicate wells in a volume of 0.2 ml. The cells were incubated at 37° C. in 5% $CO_2$ atmosphere for 24,48 and 72 hours depending on the particular experiment. After incubation, cells were counted using a cellular counter (COULTER COUNTER ZM).

| Test Compound | |
|---|---|
| Interferon gamma | 1000 U/ml |
| beta | 1000 U/ml |
| alpha | 1000 U/ml |
| mono-N-deacetyl-lyso-$GM_1$ | 100 mcg/ml |

Results

The results which are presented graphically in FIGS. 8A, 8B, 9A and 9B and numerically in Table 2 demonstrate that mono-N-deacetyl-lyso-$GM_1$ significantly reduced the proliferation of L1210 and Daudi cells in vitro, both as compared with untreated controls and with various interferons.

TABLE 2

| | 48 hours | | 72 hours | |
|---|---|---|---|---|
| | mean (S.E) | % | mean (S.E) | % |
| L1210 ($\times 10^3$) | | | | |

TABLE 2-continued

|  | 48 hours | | 72 hours | |
|---|---|---|---|---|
|  | mean (S.E) | % | mean (S.E) | % |
| Controls | 346 (37) | — | 1702 (41.76) | — |
| gamma interferon 1000 U/ml | 336 (61.6) | −2.89 | 1102 (32.4) | −35 |
| beta interferon 1000 U/ml | 310 (12.2) | −10.4 | 1059 (24) | −38 |
| alpha interferon 1000 U/ml | 294 (7.86) | −15.02 | 1114 (38) | −34 |
| mono-N-deacetyl-lyso-GM$_1$ | 177 (4) | −48.84 | 527 71.5 | −71.5 |
| DAUDI ($\times 10^3$) | | | | |
| Controls | 1250 (39.5) | — | 1984 (76.9) | — |
| gamma interferon 1000 U/ml | 1212 (69.2) | −3.04 | 2209 (44.7) | 11.3 |
| beta interferon 1000 U/ml | 1151 (42.2) | −7.92 | 2179 (34.8) | 9.8 |
| alpha interferon 1000 U/ml | 1121 (30.9) | −10.3 | 2157 (147) | 8.7 |
| mono-N-deacetyl-lyso-GM$_1$ 100 mcg/ml | 662 (55.2) | −47 | 918 (48) | −53 |

EXAMPLE 6

Effect of mono-N-deacetyl-lyso-GM$_1$ on Sarcoma 180 in vivo

Method

Groups of 10 mice (male, CD1, Carles River) were implanted subcutaneously in the right flank on day 0 with Sarcoma 180 (NCI G01143), $1.6 \times 10^5$ cells/mouse suspended in PBS Dulbecco's (GIBCO) 041-04190H). Drugs were administered by perilesional injection on days 0, 2, 4, 7, 9 and 11. Two groups of mice received mono-N-deacetyl-lyso-GM$_1$ at 100 and 10 mg/mouse and two groups received Glucan (Sigma G-5011) solubilised in FBS, also at 100 and 10 mcg/mouse.

Results

The results presented in Table 3 demonstrate that mice treated with mono-N-deacetyl-lyso-GM$_1$ were significantly protected as indicated by the fact that no deaths occurred up to 30 days from implantation of the tumour cells.

TABLE 3

| Groups | Mice | 15th day % of Mortality | 30th day % of Mortality |
|---|---|---|---|
| Controls | 10 | 30 | 60 |
| mono-N-deacetyl-lyso-GM$_1$ 100 mcg/mouse | 10 | 0 | 0 |
| mono-N-deacetyl-lyso-GM$_1$ 10 mcg/mouse | 10 | 0 | 0 |
| Glucan 100 mcg/mouse | 10 | 10 | 30 |
| Glucan 10 mcg/mouse | 10 | 10 | 10 |

EXAMPLE 7 a) Effect of preincubation of Lewis Lung Carcinoma Cells with mono-N-deacetyl-lyso-GM$_1$

Method

Lewis Lung Carcinoma Cells ($1 \times 10^6$ cells/ml) were incubated for 2 hours at 37° C. and 5% $CO_2$, with mono-N-deacetyl-lyso-GM$_1$ at concentrations of 200 mcg/ml, 100 mcg/ml and 50 mcg/ml. Groups of mice (C57BL6, male, Charles River) were challenged with the treated cells (0.1 ml/mouse i.m.). A control group received a challenge of untreated cells. The mice were observed and the time to death recorded.

Results

Figure 10:
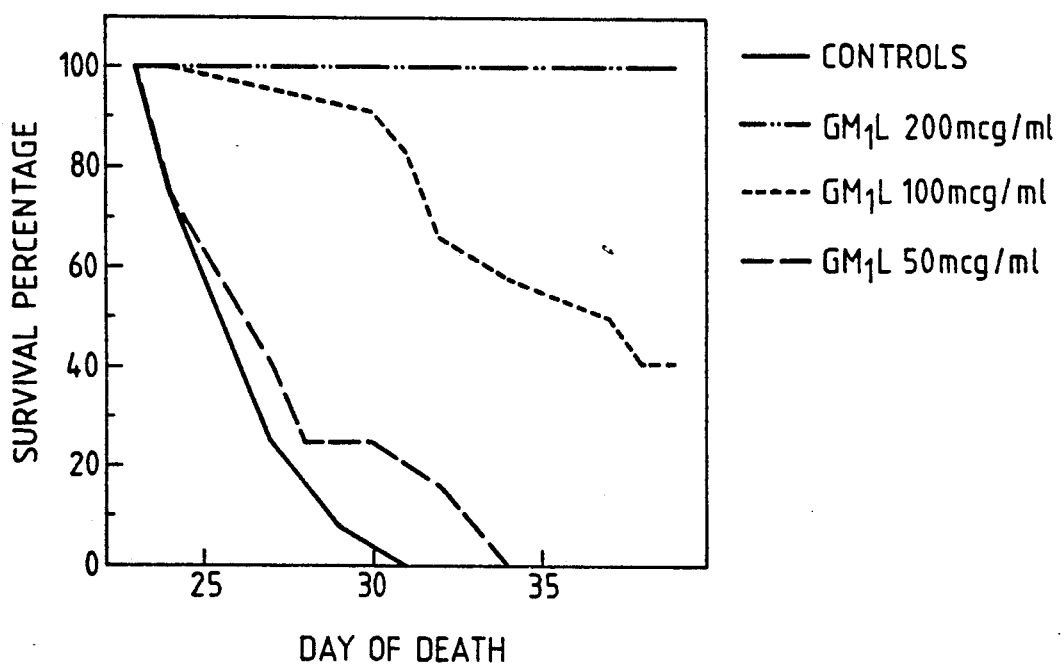

The time to death increased with the amount of mono-N-deacetyl-lyso-GM$_1$ used to pretreat the cells, indicating that mono-N-deacetyl-lyso-GM$_1$ directly reduces the oncogenicity of the cells. The results are presented graphically in FIG. 10.

b) Effect of preincubation of Lymphoma L5178Y Cells with mono-N-deacetyl-lyso-GM$_1$

Method

Lymphoma L5178Y cells ($6 \times 10^5$ cells/ml) were incubated for 90 minutes at 37° C. and 5% $CO_2$, with mono-N-deacetyl-lyso-GM$_1$ at concentrations of 100 and 50 mcg/ml. Groups of mice (CDF1, male, Charles River) were challenged with the treated cells (0.1 ml/mouse A control group received a challenge of untreated cells. The time to death was recorded.

Results

The time to death increased with the amount of mono-N-deacetyl-lyso-GM$_1$ I used to pretreat the cells, indicating that mono-N-deacetyl-lyso-GM$_1$ directly reduces the oncognecity of these cells. The results are presented graphically in FIG. 11.

EXAMPLE 8

Effect of mono-N-deacetyl-lyso GM$_1$ on Bone Marrow Graft Rejection in Irradiated Mice

Method

Three groups of mice (C57BL/6, male, 18–20 g) were given gamma irradiation, 10 Gy, at day-1. One group was given a syngeneic bone marrow graft from non-irradiated C57 BL/6 mice ($1 \times 10^6$, i.v.) at day 0. Two groups were given an allogeneic bone marrow graft from C3H male mice, ($1 \times 10^6$, i.v.) at day 0. One of these "allogeneic groups" was treated with mono-N-deacetyl-lyso-GM$_1$ 1 mg/kg i.e. at days 0, 1, 2, 3 and 4 after transplantation. A control group was irradiated but given no bone marrow graft. The mice were observed until the 35th day after transplantation and the mean survival time (MST) calculated.

Results

The results of two experiments which are presented in Tables 4 and 5 and graphically in FIGS. 12 and 13 demonstrate that mono-N-deacetyl-lyso-GM$_1$ increases the survival time of mice given an allogeneic bone marrow graft, indicating that mono-N-deacetyl-lyso-GM$_1$ prevents rejection of the graft.

TABLE 4

| Groups | MST | % of mortality |
|---|---|---|
| Controls | 14.7 | 85.7 |
| Syngeneic | 29.1 | 7.1 |
| Allogeneic | 23.0 | 57.1 |
| Allogeneic + mono-N-deacetyl-lyso-GM$_1$ | 30.7 | 7.1 |

No of animals: 14 per group

TABLE 5

| Groups | No of animals | MST |
| --- | --- | --- |
| Controls | 12 | 11.0 |
| Syngeneic | 12 | 25.5 |
| Allogeneic | 14 | 5.0 |
| Allogeneic + mono-N-deacetyl-lyso-GM$_1$ | 15 | 13.4 |

EXAMPLE 9

Effect of mono-N-deacetyl-lyso-GM$_1$ in Experimental Allergic Encephalomyelitis

Method

Antigen solution was prepared as follows:

Myelin basic protein from bovine brain M 1891 SIGMA St. Louis, USA, was dissolved in saline at a concentration of 5 mg/ml and mixed 1:1 with Freund's complete adjuvant (FCA - Difco cod 0638-60-7, Detroit USA), and 8 mg/ml of M tuberculosis H37 Ra - Difco cod 3114-33-8, Detroit USA).

Two groups of female outbred Hartley guinea pigs, eight per group, were injected with 0.1 ml of antigen solution into each hind footpad on day 0, to induce experimental allergic encephalomyelitis (EAE). One of these groups was treated daily for 5 days before challenge and for 3 days after with mono-N-deacetyl-lyso-GM$_1$, 5 mg/kg per day, i.p. A control group received FCA only.

Clinical assessment of EAE—The animals were weighed and observed daily from the first injection. The severity of EAE was graded 1 to 5 according to the criteria described by Keith & Mc Dermott, J. Jeurol Sci 1980, 46:353-364.

Clinical grading and criteria for relapse—0—No clinical signs; 1—Weight loss; 2—Mild paresis; 3—Moderate paresis; 4—Severe paresis and faecal impaction; 5—Death.

Surviving animals were euthanised by gassing, brains were fixed in 4% paraformaldehyde for histological scores, and spleens were weighed and compared to controls.

Results

Figure 14:
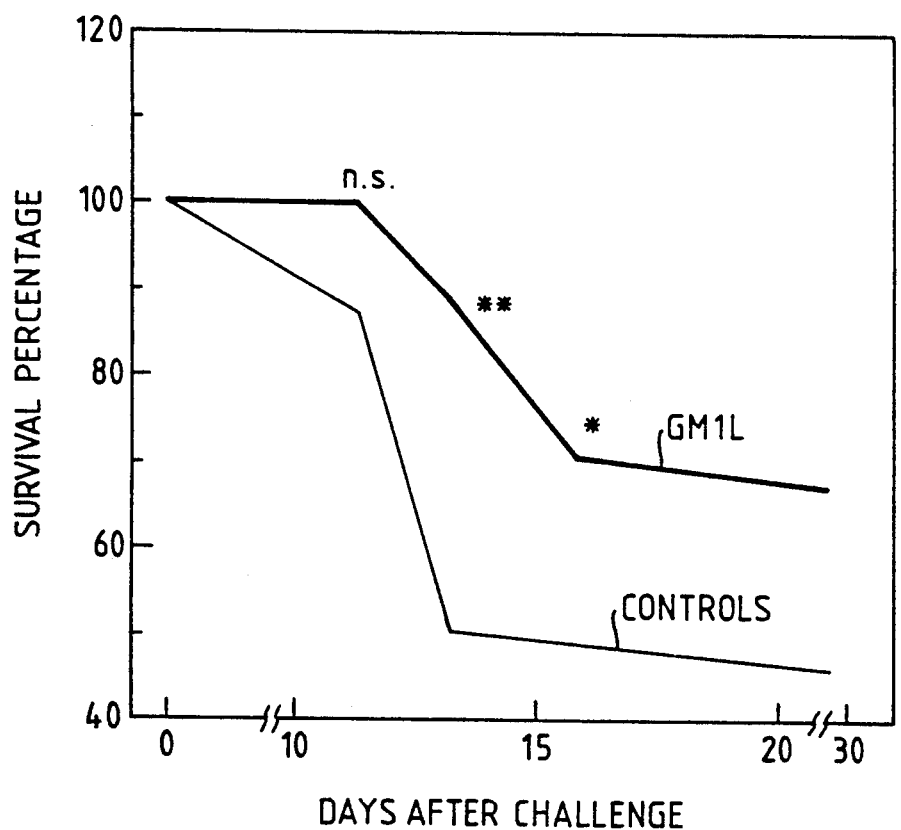
FIGS. 14 and 15 are graphs showing the results of Example 9.
Figure 15:
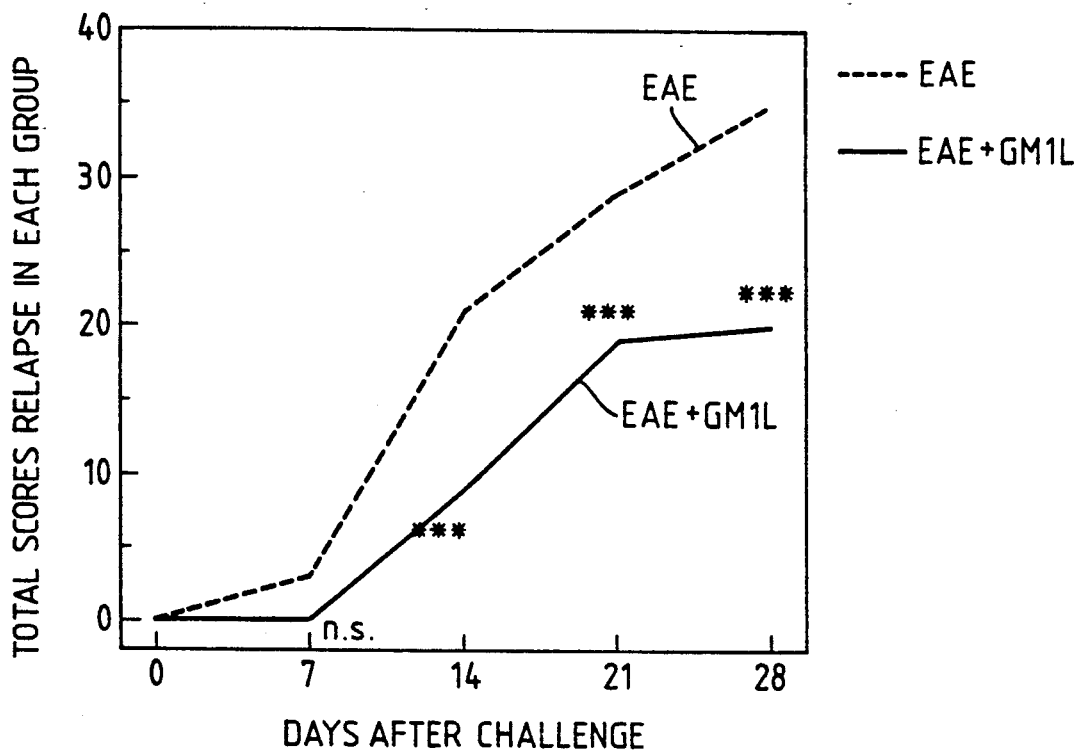

The results, which are shown in Tables 6 and 7 and FIGS. 14 and 15 demonstrate that mono-N-deacetyl-lyso-GM$_1$ reduces the clinical symptoms of EAE and increases the mortality rate.

TABLE 6

| Groups | Mortalities (dead/total) Days | | | | | | | | |
| --- | --- | --- | --- | --- | --- | --- | --- | --- | --- |
| | 10 | 11 | 12 | 13 | 14 | 15 | 16 | 17 | 18 |
| Controls | 0/8 | 0/8 | 1/8 | 4/8 | 4/8 | 4/8 | 4/8 | 4/8 | 4/8 |
| mono-N-deacetyl-lyso-GM$_1$ | 0/8 | 0/8 | 0/8 | 1/8 | 1/8 | 1/8 | 2/8 | 2/8 | 2/8 |

TABLE 7

Results of effect of mono-N-deacetyl-lyso-GM$_1$ treatment on clinical assessment of EAE.

| | Days | | | | |
| --- | --- | --- | --- | --- | --- |
| | 0 | 7 | 14 | 21 | 28 |
| Controls | 0 | 3 | 21 | 29 | 35 |
| mono-N-deacetyl-lyso-GM$_1$ | 0 | 0 | 9 | 19 | 20 |

EXAMPLE 10

Figure 16:
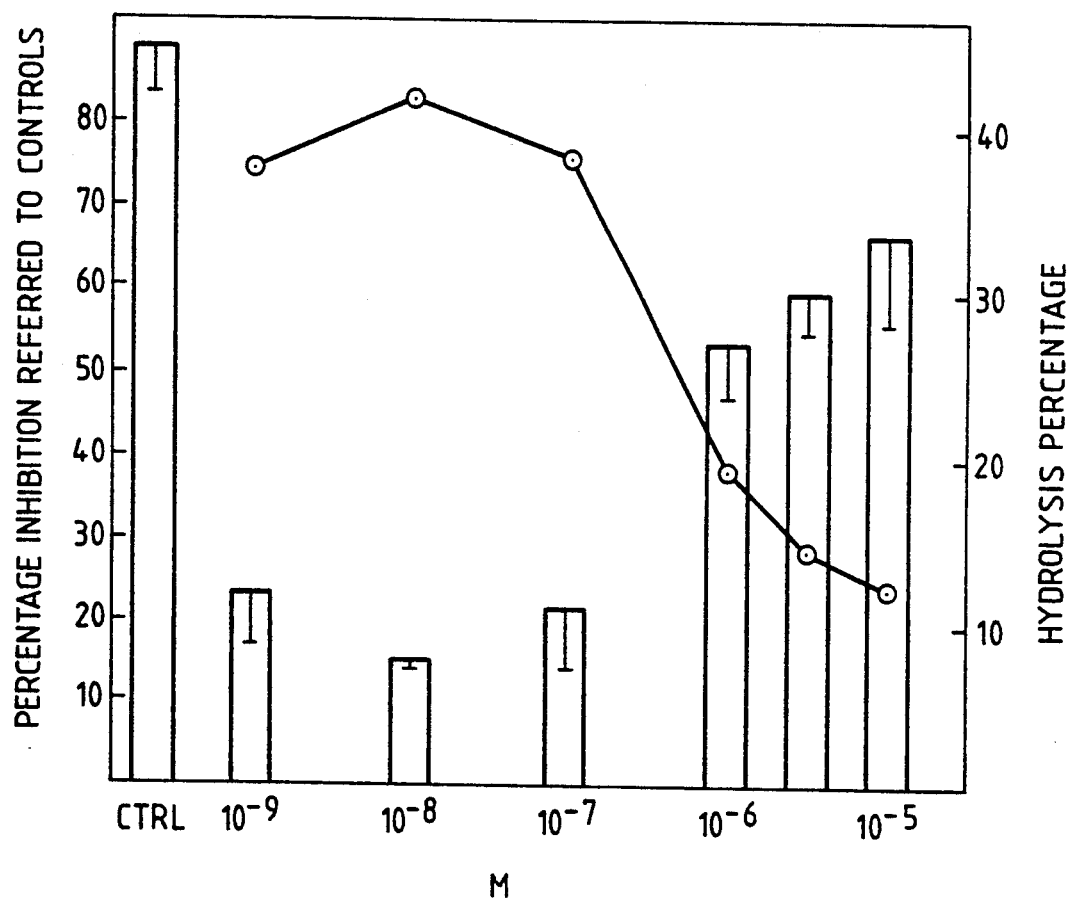
FIG. 16 is a graph showing the results of Example 10.

Effect of di-N-deacetyl-lyso-GM$_1$-C$_{20}$ on phospholipases A$_2$ (PLA$_2$) in vitro Di-N-deacetyl-lyso-GM$_1$-C$_{20}$ was tested by the method of Kremer et al, Biochemistry, 16, 3932, 1977 and found to exhibit an inhibitory effect on hog pancreas PLA$_2$ on liposomes. Results are presented in FIG. 16 below.

EXAMPLE 11

Effect of di-N-deacetyl-lyso-GM$_1$-C$_{20}$ on rabbit platelet aggregation in vivo

Method

Preparation of Platelet suspension (Platelet Rich Plasma)

Blood samples were collected from fasted New Zealand rabbits by cardiac puncture in plastic tubes containing the anticoagulant sodium citrate (final concentration 0.38%). Platelet Rich Plasma (PRP) was prepared at room temperature by centrifugation at 150 g for 20 min. and was then stored at room temperature. Platelet concentration was adjusted to 2.5 to $3 \times 10^8$/Ml.

Aggregometric Studies

Platelet aggregation was studied by the turbidimetric method of Born (Nature 194:927,1962) at a constant temperature of 37#C. Platelet suspension sample (1 ml) were stirred in the Born aggregometer and the light-transmission was monitored by continuous recording (Servogor 2s, Goers). The aggregating agent used was: Sodium arachidonate (Fluka) at the final concentrations of 20-80 mm.

Results

Figure 17:
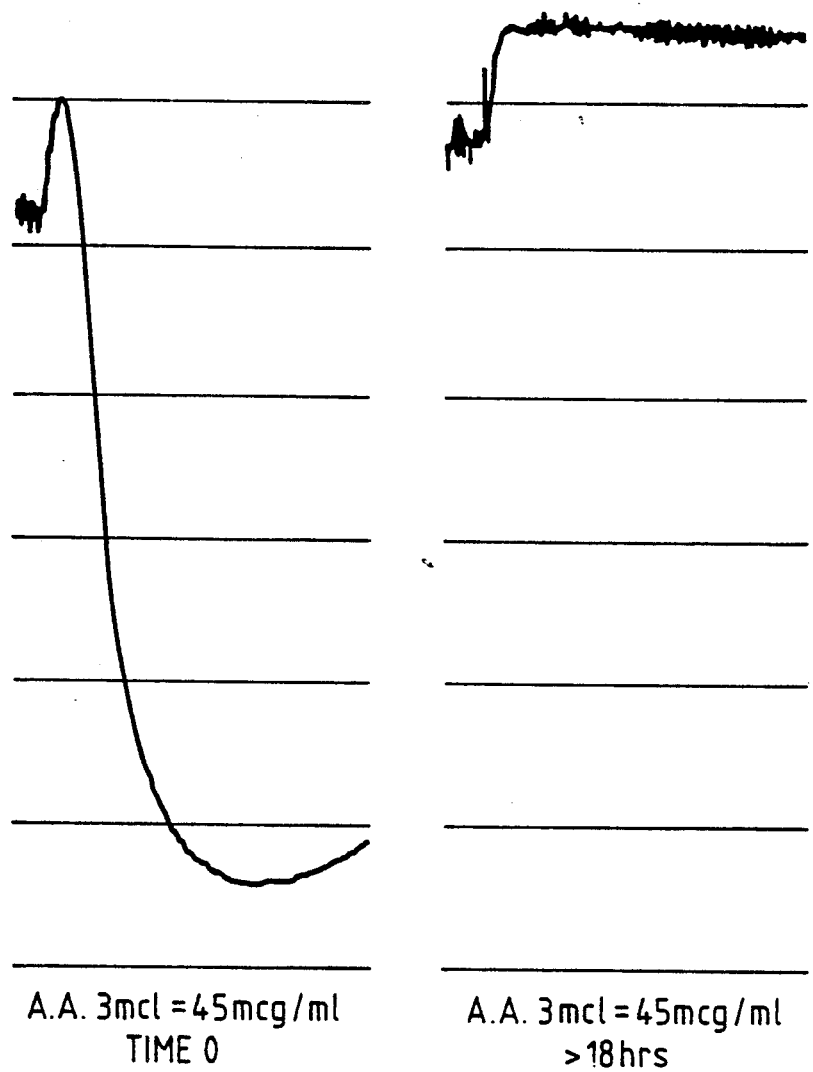
FIG. 17 is a graph showing the results of Example 11.
Figure 17:
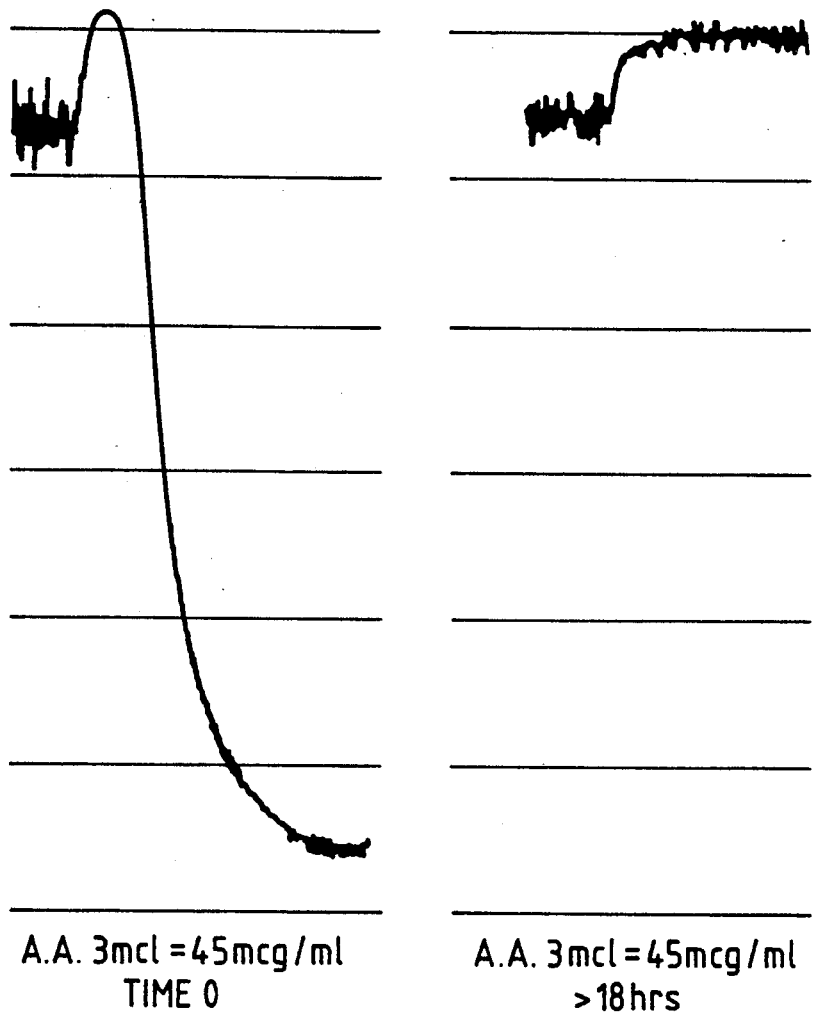

The results, which are presented graphically in FIG. 17 indicate that the compound inhibits platelet aggregation in rabbits, using arachidonic acid as agonist at doses of 0.2 and 0.13 mg/kg p.o.

EXAMPLE 12

Effect of Di-N-deacetyl-lyso-GM$_1$-C$_{20}$ on bleeding time in mice

Method

Di-N-deacetyl-lyso-GM$_1$-C$_{20}$ was administered at a dose of 0.1 mg/kg, orally to male, CD1 mice (C. River, Como, Italy) weighing 22-24 g at 96, 72, 48 and 24 hours prior to testing. The mice were anaesthetised and placed in a plastic mice restrainer (Harvard 52-0882) with several openings from one of which the animal's tail emerged. Bleeding was caused by transection of the tail, 5-6mm from the tip using a disposable surgical blade (N#18-Martin). The tails were kept vertically and placed in isotonic solution (saline) at 37#C immediately after the cut. Time in seconds was measured from the moment of the tail cut until bleeding stopped completely (no rebleeding for at least 30 sec.). Student's t-test was used for statistical analysis.

Reference: G.B. Gervasi, C. Bartoli, G. Carpita and M. Baldacci Arzneim Forsch./Drug Res.(1988) 38(II) N#9. 1268-1270.

| | Animals | mean (sec.) | % S.E. | % Incr. | P< |
|---|---|---|---|---|---|
| Control | 19 | 77.16 | 15.3 | — | — |
| Di-N-deacetyl-lyso-GM$_1$-C$_{20}$ | 19 | 180.5 | 42 | 134 | 0.029 |

EXAMPLE 13

Effect of Di-N-deacetyl-lyso-GM$_1$-C$_{20}$ on thrombin-induced thromboembolism in mice Method Di-N-deacetyl-lyso-GM$_1$-C$_{20}$ was tested according to the method of Gomi et al. (Blood Vol. 75 No. 7 1990 pp 1396-1399).

Figure 18:
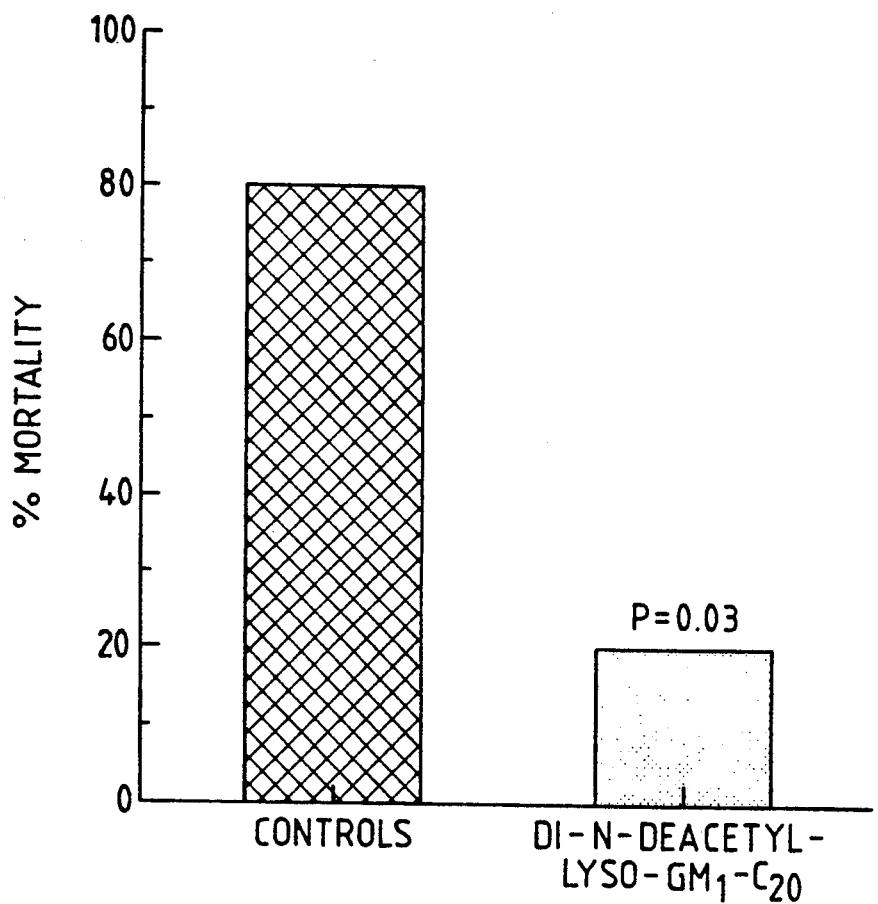
FIG. 18 is a graph showing the results of Example 12.

The results, which are presented in FIG. 18 show that the test compound significantly reduces the mortality of the mice.

EXAMPLE 14

The following represent examples of formulations which may be prepared according to the present invention.

| A. TABLET | |
|---|---|
| Compound of Formula I | 100.0 mg |
| Pregelatinised Corn Starch | 60.0 mg |
| Sodium Starch Glycollate | 20.0 mg |
| Magnesium Stearate | 4.0 mg |

The Compound of formula (I) is finely ground and intimately mixed with the powdered excipients, pregelatinised corn starch and sodium starch glycollate. The powders are wetted with purified water to form granules. The granules are dried and mixed with the magnesium stearate. The formulation is then compressed into tablets weighing approximately 184 mg each.

| B. TABLET | |
|---|---|
| Compound of formula (I) | 100.0 mg |
| Sodium Starch Glycollate | 20.0 mg |
| Lactose | 83.8 mg |
| Magnesium Stearate | 4.2 mg |
| Polyvinylpyrrolidone | 14.0 mg |

The Compound of formula (1) is finely ground and intimately mixed with the powdered excipients, sodium starch glycollate and lactose. The powders are wetted with a solution of polyvinylpyrrolidone dissolved in purified water and denatured alcohol to form granules. The granules are dried and mixed with the magnesium stearate. The formulation is then compressed into tablets weighing approximately 222 mg each.

| C. CAPSULES | |
|---|---|
| Compound of formula (I) | 100.0 mg |
| Corn Starch | 50.0 mg |
| Magnesium Stearate | 3.0 mg |

The finely divided compound of formula (I) is mixed with powdered corn starch. The dried powder is mixed with magnesium stearate and filled into hard-shell gelatin capsules.

| D. SUSPENSION | |
|---|---|
| Compound of formula (I) | 100.0 mg |
| Dispersible Cellulose | 100.0 mg |
| Glycerin | 500.0 mg |
| Sucrose | 3,500.0 mg |
| Flavouring Agent | q.s. |
| Colouring Agent | q.s. |
| Preserving Agent | 0.1% |
| Purified Water q.s. to | 5.0 ml |

The compound of formula (I) is suspended in the glycerin and a portion of the purified water. The sucrose and preserving agent are dissolved in another portion of hot purified water, and then the colouring agent is added and dissolved, followed by the dispersible cellulose. The two preparations are mixed and cooled before the flavouring agent is added. Purified water is added to final volume. The resulting suspension is throughly mixed.

| E. IV INJECTION | |
|---|---|
| Compound of formula (I) | 5.0 mg |
| Hydrochloric Acid | as needed for pH adjustment |
| Water for Injections | q.s. to 10 ml |

The compound of formula (I) is added to a portion of the Water for Injections. The pH is adjusted with hydrochloric acid to dissolve the compound. Water for Injections is added to final volume and solution is complete after thorough mixing. The solution is sterilised by filtration through a 0.22 micrometer membrane filter and aseptically filled into sterile 10 ml ampoules or vials.

We claim:

1. An N-deacetyl-lysoganglioside or a physiologically acceptable salt thereof in substantially pure form of the formula:

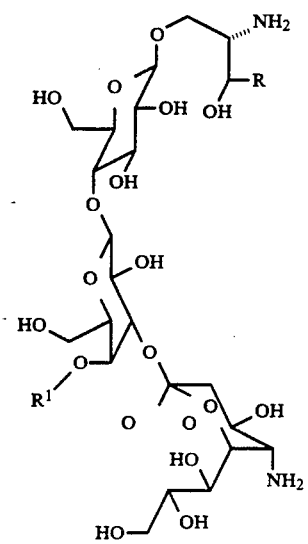
wherein
R represents —CH=CH(CH₂)ₙCH₃ or —CH₂CH₂(CH)₂)ₙCH₃;
n is 12 or 14;
R¹ represents
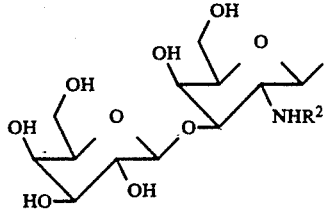
and
R² represents hydrogen.
2. An N-deacetyl-lysoganglioside according to claim 1 wherein n is 14 or pharmaceutically acceptable salt thereof.
3. An N-deacetyl-lysoganglioside according to claim 1 wherein n is 12 or pharmaceutically acceptable salt thereof.
* * * * *